(12) United States Patent
Vu et al.

(10) Patent No.: US 7,550,608 B2
(45) Date of Patent: Jun. 23, 2009

(54) PROCESSES FOR THE PREPARATION OF DOCETAXEL

(75) Inventors: Phong Vu, Little Falls, NJ (US); Robert A. Holton, Tallahassee, FL (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 47 days.

(21) Appl. No.: 11/449,048

(22) Filed: Jun. 8, 2006

(65) Prior Publication Data

US 2006/0281932 A1 Dec. 14, 2006

Related U.S. Application Data

(60) Provisional application No. 60/788,943, filed on Apr. 4, 2006, provisional application No. 60/724,527, filed on Oct. 7, 2005, provisional application No. 60/708,931, filed on Aug. 17, 2005, provisional application No. 60/708,929, filed on Aug. 17, 2005, provisional application No. 60/689,425, filed on Jun. 10, 2005.

(51) Int. Cl.
C07D 305/00 (2006.01)
C07D 407/00 (2006.01)

(52) U.S. Cl. .................. 549/510; 549/511; 549/214

(58) Field of Classification Search .......... 549/510, 549/214, 511
See application file for complete search history.

(56) References Cited

U.S. PATENT DOCUMENTS

| 4,924,011 | A |  | 5/1990 | Denis et al. |
|---|---|---|---|---|
| 5,015,744 | A |  | 5/1991 | Holton |
| 5,175,315 | A |  | 12/1992 | Holton |
| 5,399,726 | A |  | 3/1995 | Holton et al. |
| 5,430,160 | A |  | 7/1995 | Holton |
| 5,466,834 | A |  | 11/1995 | Holton |
| 5,539,103 | A | * | 7/1996 | Holton ............... 540/354 |
| 5,668,270 | A | * | 9/1997 | Bauman et al. ......... 536/26.71 |
| 5,723,634 | A |  | 3/1998 | Holton |
| 5,760,251 | A | * | 6/1998 | Gao et al. ............... 549/510 |
| 5,763,477 | A |  | 6/1998 | Duvvuri et al. |
| 6,191,287 | B1 |  | 2/2001 | Holton et al. |
| 6,225,463 | B1 |  | 5/2001 | de Vos et al. |
| 6,265,587 | B1 | * | 7/2001 | Chanteloup et al. ........ 548/237 |
| 6,562,962 | B2 | * | 5/2003 | Holton ............... 540/357 |
| 6,825,365 | B2 |  | 11/2004 | Chanteloup et al. |

FOREIGN PATENT DOCUMENTS

| EP | 0 400 971 | A2 | 5/1990 |
|---|---|---|---|
| EP | 0 617 034 | A1 | 9/1994 |
| WO | 94/18164 | A1 | 8/1994 |
| WO | 97/07110 | A1 | 2/1997 |
| WO | 97/15562 | A1 | 5/1997 |
| WO | 02/085878 | A1 | 10/2002 |
| WO | 2004/013096 | A2 | 2/2004 |
| WO | 2006/004898 | A2 | 1/2006 |
| WO | 2006/089207 | A2 | 8/2006 |

OTHER PUBLICATIONS

Office Action dated Oct. 10, 2007, U.S. Appl. No. 11/449,075, 4 pages.
Tarrant, J.G. et al., "Synthesis and Biological Activity of Macrocyclic Taxane Analogues," Bioorganic & Medicinal Chemistry Letters, 2004, pp. 2555-2558, vol. 14.
Gelest, Inc. Catalog, Silicon-Based Blocking Agents; Reagents For: Functional Group Protection, Synthesis, Derivitization, 2004, 29 pages.
Greene, et al., "Protective Groups In Organic Synthesis," John Wiley & Sons, New York, 2007, pp. 165-166.
Corriu, R.J.P., "Hypervalent Species of Silicon: Structure and Reactivity," Journal of Organometallic Chemistry, 1990, pp. 81-106, vol. 400.
Denis, J.-N., et al., "A Highly Efficient, Practical Approach to Natural Taxol," J. Am. Chem. Soc., 1988, pp. 5917-5919, vol. 110, No. 17.
Grobe, J., et al., "Atrane Analogous Compounds of Type Me2Si-Y-M'Me2(OCH2CH2)NME (-O-CH3-CH2-) (I)," Z. Naturforsch., B Anorg. Chem., Org. Chem., 1983, pp. 269-279, vol. 38B, No. 3.
Gueritte-Voegelein, F., et al., "Chemical Studies of 10-Deacetyl Baccatin III. Hemisynthesis of Taxol Derivatives," Tetrahedron, 1986, pp. 4451-4460, vol. 42, No. 16.
Holton, R.A., et al., "Selective Protection of the C(7) and C(10) Hydroxyl Groups in 10-Deacetyl Baccatin III," Tetrahedron Letters, 1998, pp. 2883-2886, vol. 39.
Office Action dated Feb. 16, 2007, U.S. Appl. No. 11/449,075, 13 pages.
Office Action dated Jun. 21, 2007, U.S. Appl. No. 11/449,075, 16 pages.
Uhlig, W., et al., "Synthesis and Reactivity of Triflate Substituted Siloxane Derivatives," Z. Anorg. Allg. Chem., 1994, pp. 939-943, vol. 620.
Jagtap, P. G., et al., "A Facile N-Debenzoylation of Paclitaxel: Conversion of Paclitaxel to Docetaxel," Tetrahedron Letters, 1999, pp. 189-192, vol. 40.
International Search Report, PCT/US2006/022335, dated Dec. 27, 2006, 4 pages.
Commercon, A., et al., "Improved Protection and Esterification of a Precursor of the Taxotere® and Taxol Side Chains", Tetrahedron Letters, 1992, pp. 5185-5188, vol. 33, No. 36.
Denis, J-N., et al., "A Highly Efficient, Practical Approach to Natural Taxol", J. Am. Chem. Soc., 1988, pp. 5917-5919, vol. 110, No. 17.
Farina, V., et al., "A Simple Chiral Synthesis of the Taxol Side Chain", Synlett, Sep. 1992, pp. 761-763, vol. 9.
Hart, D. J., et al., "The Ester Enolate-Imine Condensation Route to β-Lactams", Chem. Rev., 1989, pp. 1447-1465, vol. 89, No. 7.
Mangatal, L., et al., "Application of the Vicinal Oxyamination Reaction with Asymmetric Induction to the Hemisynthesis of Taxol and Analogues", Tetrahedron, 1989, pp. 4177-4190, vol. 45, No. 13.
Senilh, V., et al., "Analyse Structurale et etude Biochimique de produits isoles de l'If: Taxus baccata L. (Taxacees)", C.R. Acad. Sci. Paris, IT, 1981, pp. 501-503, vol. 293, No. 7.
van Tilburg, E. W., et al., "Radiosynthesis of [11C]docetaxel", Journal of Labelled Compounds and Radiopharmaceuticals, 2004, pp. 763-777, vol. 47.

* cited by examiner

*Primary Examiner*—Janet L. Andres
*Assistant Examiner*—Raymond Covington
(74) *Attorney, Agent, or Firm*—Bryan Cave LLP

(57) ABSTRACT

The present invention provides processes for the production of docetaxel. Docetaxel is produced by protecting the C(7) and the C(10) hydroxy groups of 10-DAB with a bridging silicon-based protecting group. The resulting 7,10-protected 10-DAB derivative is then derivatized and deprotected to form docetaxel.

32 Claims, No Drawings

PROCESSES FOR THE PREPARATION OF DOCETAXEL

REFERENCE TO RELATED APPLICATIONS

This application claims priority from U.S. provisional application Ser. No. 60/689,425, filed on Jun. 10, 2005; U.S. provisional application Ser. No. 60/708,929, filed on Aug. 17, 2005; U.S. provisional application Ser. No. 60/708,931, filed on Aug. 17, 2005; U.S. provisional application Ser. No. 60/724,527, filed on Oct. 7, 2005; and U.S. provisional application Ser. No. 60/788,943, filed on Apr. 4, 2006.

BACKGROUND OF THE INVENTION

The present invention generally relates to processes for preparing docetaxel. More specifically, the present invention relates to processes for the preparation of docetaxel including the protection of the C(7) and the C(10) hydroxy groups of 10-deacetylbaccatin III (10-DAB) using a bridging silicon-based protecting group.

10-DAB (1), which is extracted from the needles of the English yew (*taxus baccata* L.), is a key starting material in the production of taxol (also known as paclitaxel) and docetaxel (Taxotere®), both of which are potent anticancer agents.

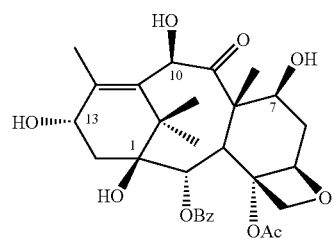

(1)

Conversion of 10-DAB to a cytotoxically active taxane requires selective derivatization of the C(13) hydroxy group to form a C(13) ester side chain. Because 10-DAB is a polyol and because each of these hydroxy groups is not equally reactive under a defined set of conditions, preparation of taxol or docetaxel from 10-DAB typically requires selective protection and/or derivatization of the C(7) and the C(10) hydroxy groups before the C(13) side chain is attached.

Early strategies for the preparation of taxol, docetaxel and other taxanes from 10-DAB were based on the observation of Senilh et al. (*C.R. Acad. Sci. Paris, IT,* 1981, 293, 501) that the relative reactivity of the four hydroxy groups of 10-DAB toward acetic anhydride in pyridine is C(7)-OH>C(10)-OH>C(13)-OH>C(1)-OH. Denis et al. reported (*J. Am. Chem. Soc.,* 1988, 110, 5917) selective silylation of the C(7) hydroxy group of 10-DAB with triethylsilyl chloride in pyridine to give 7-triethylsilyl-10-deacetyl baccatin (III) in 85% yield.

More recently, Holton et al. disclosed in U.S. Pat. No. 6,191,287 that the relative reactivity toward acetic anhydride as between C(7) and C(10) is different in the presence of a Lewis acid than it is in the presence of base. Holton et al. described processes for the selective derivatization of the C(7) or the C(10) hydroxy group of 10-DAB and other taxanes, wherein the C(10) hydroxy group may be protected or derivatized prior to the C(7) hydroxy group. Specifically, Holton et al. described a process for acylating or silylating the C(10) hydroxy group prior to acylating, silylating, or ketalizing the C(7) hydroxy group.

SUMMARY OF THE INVENTION

Among the various aspects of the present invention is the provision of processes for preparing docetaxel in fewer steps than previously known processes. Among the steps, the processes include protecting the C(7) and the C(10) hydroxy groups of 10-deacetylbaccatin III (10-DAB) with a bridging silicon-based protecting group and derivatizing the 7,10-protected 10-DAB derivative, wherein the protection, derivatization, and subsequent deprotection steps proceed in relatively high yield.

Briefly, therefore, the present invention is directed to a process for the preparation of docetaxel, the process comprising:

(a) protecting the C(7) and the C(10) hydroxy groups of 10-deacetylbaccatin III (10-DAB) with a bridging silicon-based protecting group to form a 10-DAB derivative;

(b) further derivatizing the 10-DAB derivative, the further derivatization comprising treating the 10-DAB derivative with a β-lactam side chain precursor to form a 10-DAB derivative having a side chain; and (c) deprotecting the product of step (b) to form docetaxel.

Other objects and features will be in part apparent and in part pointed out hereinafter.

DETAILED DESCRIPTION OF THE INVENTION

In accordance with the process of the present invention, it has been discovered that docetaxel may be prepared by, among other steps, selectively and simultaneously protecting the C(7) and the C(10) hydroxy groups of 10-deacetylbaccatin III (10-DAB) (1) with a bridging silicon-based protecting group. The resulting 7,10-protected 10-DAB derivative is then derivatized and deprotected to produce docetaxel.

Generally speaking, the bridging silicon-based protecting group used to protect the C(7) and the C(10) hydroxy groups of 10-DAB (1) corresponds to Formula (2):

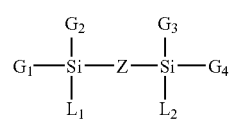

(2)

wherein $G_1$, $G_2$, $G_3$, and $G_4$ are independently hydrocarbyl, substituted hydrocarbyl, alkoxy, or heterocyclo;

$L_1$ and $L_2$ are independently amine, halide, or sulfonate leaving groups;

Z is hydrocarbyl, substituted hydrocarbyl, heterocyclo, —[O—Si($Z_{10}$)($Z_{11}$)-]$_n$O—, or —O—;

each $Z_{10}$ and $Z_{11}$ is independently hydrocarbyl; and n is 1 or 2.

In one embodiment in which the bridging silicon-based protecting group corresponds to Formula (4), Z is hydrocarbyl. In one such embodiment, Z is —(CH$_2$)$_y$—, wherein y is a positive integer from 1 to about 8. More preferably in this embodiment, y is 1 to about 4.

In another embodiment in which the bridging silicon-based protecting group corresponds to Formula (4), Z is substituted hydrocarbyl. In one particular embodiment, Z is -[($Z_{12}$)-

$(Z_{13})]_k$-$[(Z_{14})]_m$-, wherein $Z_{12}$, $Z_{13}$, and $Z_{14}$ are each independently —$(CH_2)_y$—, —O—, —S—, or —N—, provided that at least one of $Z_{12}$ and $Z_{13}$ is —O—, —S—, or —N—, k is a positive integer from 1 to about 4, m is 0 or 1, and y is a positive integer from 1 to about 4.

In yet another embodiment in which the bridging silicon-based protecting group corresponds to Formula (2), Z is —[O—Si$(Z_{10})(Z_{11})$-]$_n$O— or —O—, wherein n is 1 or 2. That is, when n is 1, Z is —O—Si$(Z_{10})(Z_{11})$-O—; and when n is 2, Z is —O—Si$(Z_{10})(Z_{11})$-O—Si$(Z_{10})(Z_{11})$-O—. When n is either 1 or 2, each $Z_{10}$ and each $Z_{11}$ is independently hydrocarbyl (that is, the two $Z_{10}$ substituents need not be the same hydrocarbyl moiety and the two $Z_{11}$ substituents need not be the same hydrocarbyl moiety). In some embodiments, $Z_{10}$ and $Z_{11}$ are alkyl. In other embodiments, $Z_{10}$ and $Z_{11}$ are lower alkyl having from about 1 to about 4 carbon atoms. In still other embodiments, $Z_{10}$ and $Z_{11}$ are methyl.

In any one of the various embodiments described above (i.e., when Z is —$(CH_2)_y$—, -$[(Z_{12})$-$(Z_{13})]_k$-$[(Z_{14})]_m$-, —[O—Si$(Z_{10})(Z_{11})$-]$_n$O—, or —O—), $G_1$, $G_2$, $G_3$, and $G_4$ are independently hydrocarbyl, substituted hydrocarbyl, alkoxy, or heterocyclo. In some embodiments, $G_1$, $G_2$, $G_3$, and $G_4$ are independently substituted or unsubstituted alkyl, alkyenyl, alkynyl, aryl, heteroaryl, or cycloalkyl. In other embodiments, $G_1$, $G_2$, $G_3$, and $G_4$ are independently linear or branched alkyl or alkenyl having from about 1 to about 4 carbon atoms, cycloalkyl having from about 1 to about 6 carbon atoms, or phenyl. In still other embodiments, $G_1$, $G_2$, $G_3$, and $G_4$ are independently methyl, ethenyl, isopropyl, phenyl, or cyclopentyl. When any one or more of $G_1$, $G_2$, $G_3$, and $G_4$ is alkoxy, it is preferably $C_1$-$C_6$ alkoxy.

In any one or more of the embodiments described above, $L_1$ and $L_2$ are each independently amine, halide, or sulfonate leaving groups. In one embodiment, $L_1$ and $L_2$ are halide leaving groups. For example, $L_1$ and $L_2$ may be independently chloro, fluoro, bromo, or iodo. Alternatively, $L_1$ and $L_2$ may be amine leaving groups. For example, $L_1$ and $L_2$ may be independently cyclic amines or dialkyl amines such as imidazole, diethylamine, diisopropylamine, and the like. In another alternative example, $L_1$ and $L_2$ may be sulfonate leaving groups. For example, $L_1$ and $L_2$ may be independently tosylate, triflate, mesylate, and the like.

In one specific embodiment, therefore, $L_1$ and $L_2$ are halide leaving groups; $G_1$, $G_2$, $G_3$, and $G_4$ are independently substituted or unsubstituted alkyl, alkenyl, alkynyl, aryl, heteroaryl, or cycloalkyl; Z is —$(CH_2)_y$—; and y is a positive integer from 1 to about 8.

In another specific embodiment, $L_1$ and $L_2$ are chloro leaving groups; $G_1$, $G_2$, $G_3$, and $G_4$ are independently linear or branched alkyl or alkenyl having from about 1 to about 4 carbon atoms, cycloalkyl having from 1 to about 6 carbon atoms, or phenyl; Z is —$(CH_2)_y$—; and y is a positive integer from 1 to about 4.

In a third specific embodiment, $L_1$ and $L_2$ are halide leaving groups; $G_1$, $G_2$, $G_3$, and $G_4$ are independently substituted or unsubstituted alkyl, alkenyl, alkynyl, aryl, heteroaryl, or cycloalkyl; Z is —[O—Si$(Z_{10})(Z_{11})$-]$_n$O— or —O—; n is 1 or 2; and $Z_{10}$ and $Z_{11}$ are alkyl.

In a fourth specific embodiment, $L_1$ and $L_2$ are chloro leaving groups; $G_1$, $G_2$, $G_3$, and $G_4$ are independently linear or branched alkyl or alkenyl having from about 1 to about 4 carbon atoms, cycloalkyl having from about 1 to about 6 carbon atoms, or phenyl; and Z is —O—.

In any one of the four preceding specific embodiments $L_1$ and $L_2$ may be, instead of a halide (or, more specifically, chloro), any other suitable functionally reactive leaving group. For example, $L_1$ may be chloro while $L_2$ could be a different leaving group such as a different halide, amine, or sulfonate leaving group. Alternatively, each of $L_1$ and $L_2$ could be, independently, any other combination of amine, halide, or sulfonate leaving groups.

Certain particularly preferred bridging silicon-based protecting groups are identified in Table 1 (each of which and other suitable bridging silicon-based protecting groups for use in the process of the present invention being commercially available from Gelest, Inc., Morrisville, Pa.):

TABLE 1

| Formula Name | Structure |
|---|---|
| 1,3-dichlorotetramethyldisiloxane | 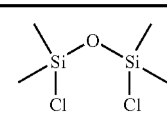 |
| 1,5-dichlorohexamethyltrisiloxane | 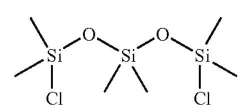 |
| 1,7-dichlorooctamethyltetrasiloxane | 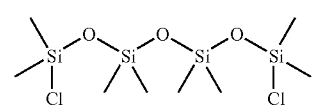 |
| 1,3-dichloro-1,3-diphenyl-1,3-dimethyldisiloxane | 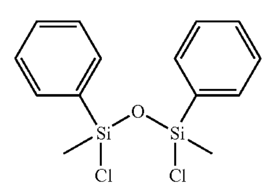 |

TABLE 1-continued

| Formula Name | Structure |
|---|---|
| 1,3-dichlorotetraphenyldisiloxane | 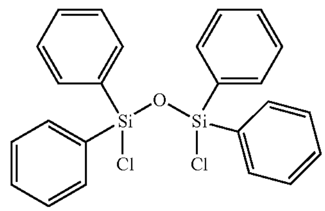 |
| 1,3-divinyl-1,3-dimethyl-1,3-dichlorodisiloxane | 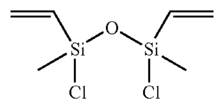 |
| 1,1,3,3-tetracyclopenyldichlorodisiloxane | 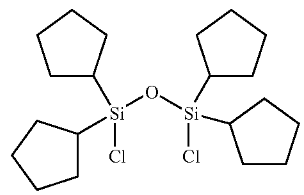 |
| 1,1,3,3-tetraisopropyl-1,3-dichlorodisiloxane | 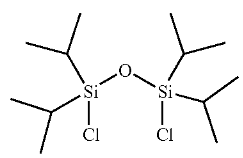 |
| 1,2-bis(chlorodimethylsilyl)ethane | 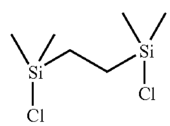 |
| 1,3-bis(chlorodimethylsilyl)propane | 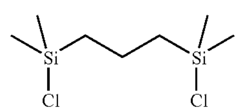 |
| 1,6-bis(chlorodimethylsilyl)hexane | 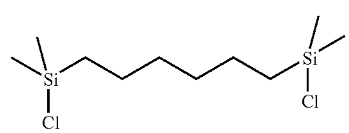 |
| 1,8-bis(chlorodimethylsilyl)octane | 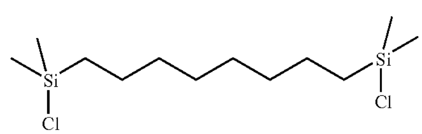 |

It will be understood by one of ordinary skill in the art that each of the bridging silicon-based protecting groups identified in Table 1 could have, instead of chloro, other suitable functionally reactive leaving groups attached to the silyl atom at each end of the bridging silicon-based protecting group. For example, the leaving group at one end could be chloro while the leaving group at the other end could be a different leaving group such as a different halide, amine, or sulfonate leaving group. Alternatively, each of the two leaving groups could be, independently, any other combination of amine, halide, or sulfonate leaving groups.

The bridging silicon-based protecting groups described above are used with 10-DAB (1), whether obtained from natural or synthetic sources, to protect the C(7) and the C(10) hydroxy groups of 10-DAB (1). The C(7) and C(10) protection occurs prior to the derivatization of 10-DAB (1), such as the coupling reaction between a β-lactam side chain precursor and 10-DAB to introduce a C(13) side chain onto 10-DAB, described in detail below. Once 10-DAB (1) has been suitably derivatized to provide the C(13) side chain having the various substituents carried by docetaxel, the various protecting groups may be removed (i.e., deprotected) to produce docetaxel.

As noted above, the processes of the present invention include the attachment of a side chain at the C(13) position of 10-DAB (1) by treatment with a β-lactam side chain precursor. In a preferred embodiment, the β-lactam side chain precursor corresponds to Formula (3):

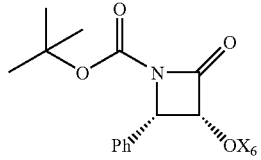

(3)

wherein $X_6$ is a hydroxy protecting group. Appropriate hydroxy protecting groups include, for example, acetals such as tetrahydropyranyl (THP), methoxymethyl (MOM), 1-ethoxyethyl (EE), 2-methoxy-2-propyl (MOP), 2,2,2-trichloroethoxymethyl, 2-methoxyethoxymethyl (MEM), 2-trimethylsilylethoxymethyl (SEM), and methylthiomethyl (MTM). Alternatively, the hydroxy protecting group may be a silyl protecting group having bulky alkyl groups such as trimethylsilyl, triethylsilyl, tributylsilyl, triisopropylsilyl, dimethylisopropylsilyl, diphenylmethylsilyl, dimethylphenylsilyl, and the like.

Generally, the β-lactam side chain precursors suitable for use in the processes of the present invention can be made as known in the art. In various embodiments, however, β-lactam side chain precursors generally corresponding to Formula (3) may be prepared according to the various pathways illustrated in Reaction Scheme 1.

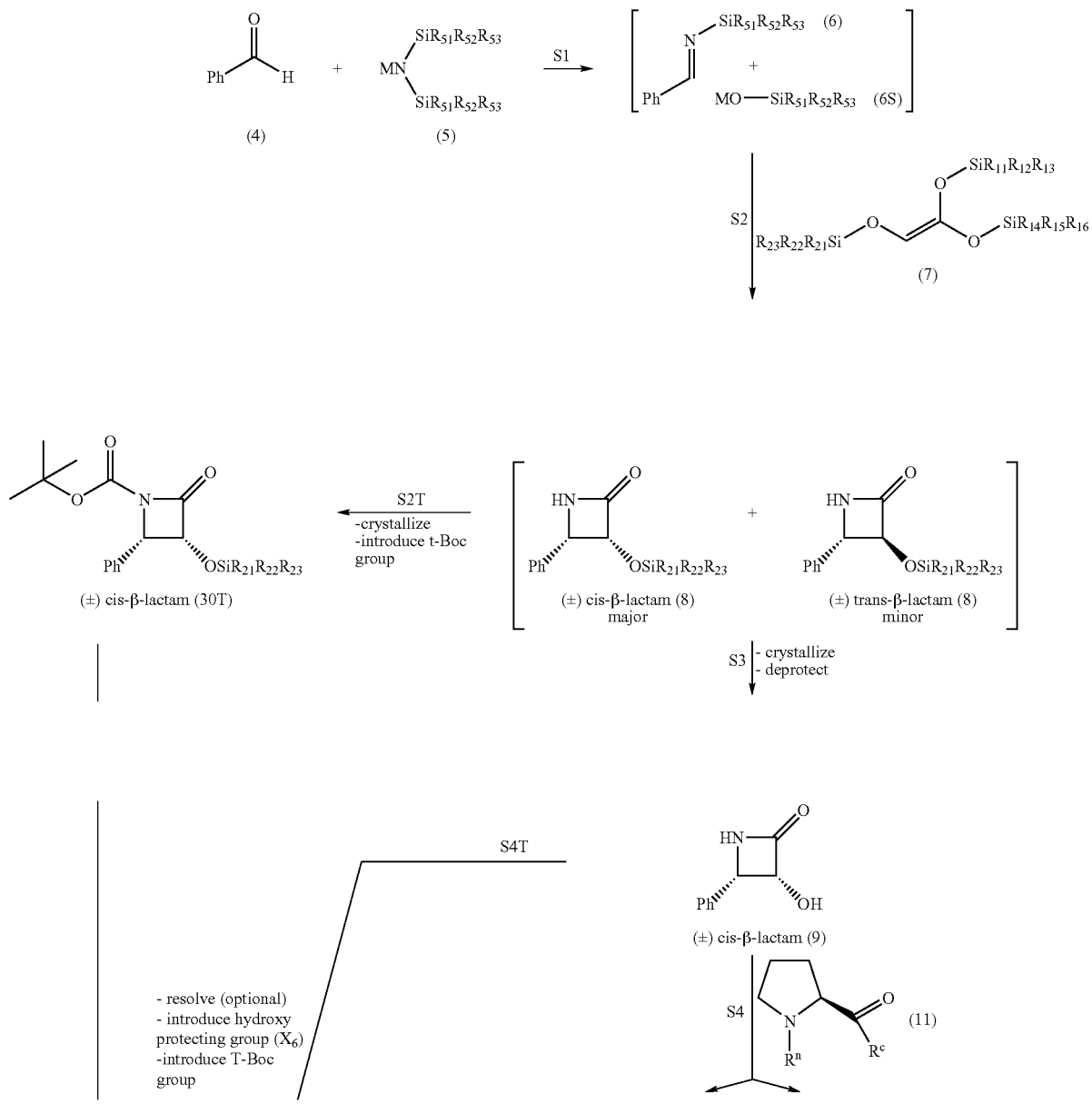

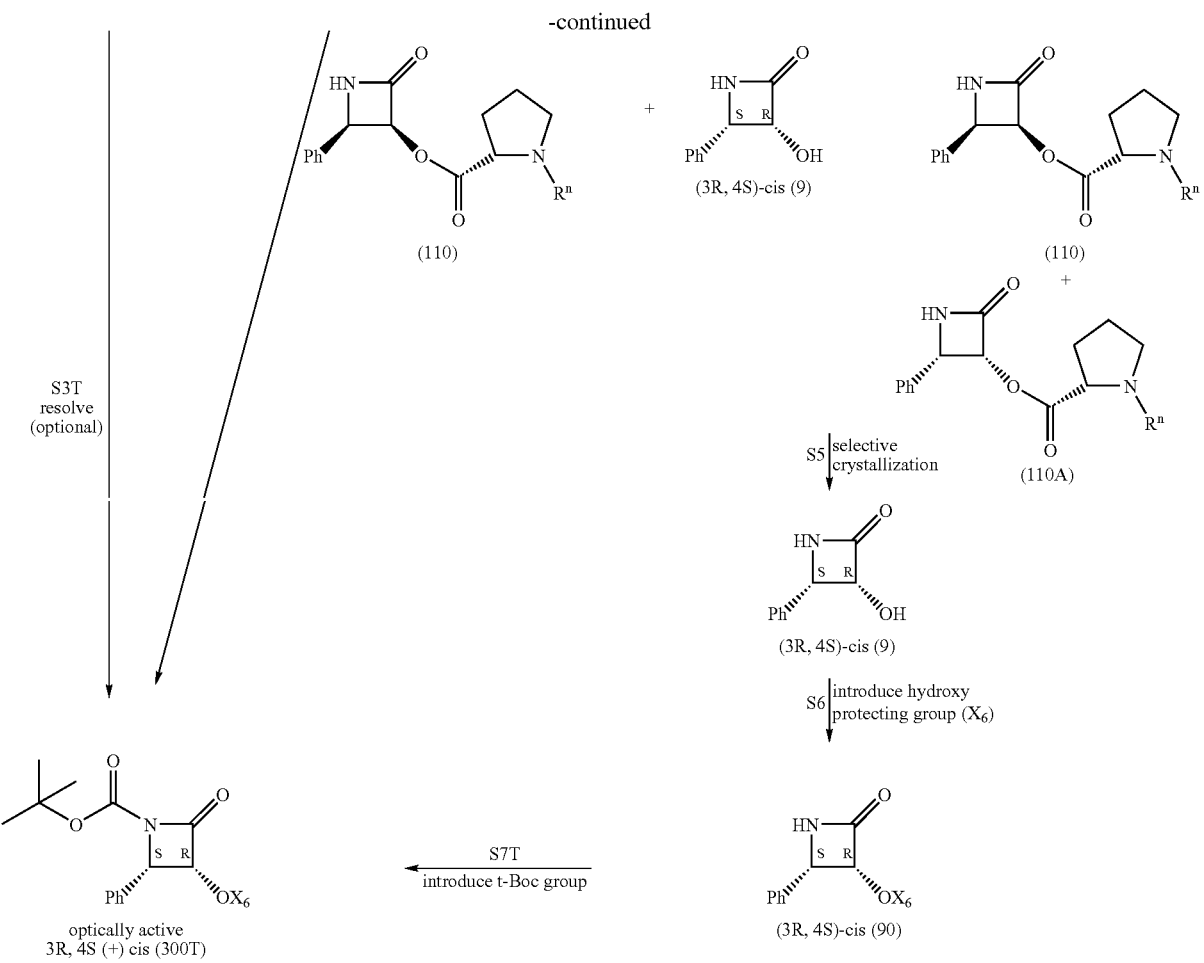

In Stage 1 of Reaction Scheme 1, benzaldehyde (4) is reacted with a disilazide (5) in the presence of a polar aprotic solvent (e.g., tetrahydrofuran (THF)) to form a phenyl-substituted imine (6) along with an equivalent of a metal siloxide (6S). In various embodiments, M is an alkali metal and $R_{51}$, $R_{52}$, and $R_{53}$ are independently alkyl, aryl, or aralkyl. Preferably, $R_{51}$, $R_{52}$ and $R_{53}$ are methyl. In one preferred embodiment, disilazide (5) is lithium- or sodium-hexamethyldisilazide (i.e., LHMDS or NaHMDS).

In Stage 2, the imine (6) is treated with a ketene acetal (7). In various embodiments, $R_{21}$, $R_{22}$, and $R_{23}$ are independently alkyl, aryl, or aralkyl. Preferably, $R_{21}$, $R_{22}$, and $R_{23}$ are methyl. Further, $R_{11}$, $R_{12}$, $R_{13}$, $R_{14}$, $R_{15}$, and $R_{16}$ are independently alkyl, provided that either $R_{11}$, $R_{12}$, and $R_{13}$ or $R_{14}$, $R_{15}$, and $R_{16}$ are methyl. In one preferred embodiment, each of $R_{11}$, $R_{12}$, $R_{13}$, $R_{14}$, $R_{15}$, $R_{16}$, $R_{21}$, $R_{22}$, and $R_{23}$ are methyl. According to this embodiment, the ketene acetal (7) is tris (trimethylsilyloxy)ethane, which is available commercially.

The reactions of Stage 1 and Stage 2 form an N-unsubstituted β-lactam. More specifically, the β-lactam ring-forming reaction in Stage 2 is diastereoselective and (±)-cis-β-lactam (8) and (±)-trans-β-lactam (8) isomers are formed preferentially in about a 5:1 cis:trans ratio. Following the formation of the N-unsubstituted β-lactam, the (±)-cis-β-lactam is crystallized from the isomeric mixture (e.g., using ethyl acetate) and derivatized according to various pathways to form β-lactam side chain precursors carrying appropriate substituents for the preparation of docetaxel (e.g., β-lactam side chain precursors generally corresponding to Formula (3), above). In various embodiments it may also be desirable to resolve the enantiomeric mixture of (±)-cis-β-lactam (8) into its enantiomers. Various pathways for resolving and/or derivatizing the N-unsubstituted β-lactams are described in detail below.

According to one pathway the silyl moiety (i.e., —$SiR_{21}R_{22}R_{23}$) that ends up in the C(3) position of the isomeric N-unsubstituted β-lactam remains in that position throughout the various steps used to form suitable β-lactam side chain precursors for use in the processes of the present invention.

As shown in Stage 2T, the (±)-cis-β-lactam isomer is crystallized from the isomeric mixture of (±)-cis- and (±)-trans-β-lactams (e.g., using ethyl acetate), and the (±)-cis-β-lactam is derivatized by introducing a tert-butoxycarbonyl (t-Boc) group (e.g., using di-tert-butyldicarbonate) to the —NH moiety, resulting in the formation of (±)-cis-β-lactam (30T). In various embodiments, (±)-cis-β-lactam (30T) may be utilized as the β-lactam side chain precursor in the process of the present invention. Alternatively, in other embodiments it may be desirable to resolve the enantiomeric mixture of (±)-cis-β-lactam (30T) into its enantiomers, as shown in Stage 3T. The resolution in Stage 3T may be performed by various methods known in the art such as, for example, enzymatic resolution, to form optically active (3R,4S)-cis-β-lactam (300T), wherein $X_6$ is —$SiR_{21}R_{22}R_{23}$ (i.e., the silyl moiety that ends up in the C(3) position remains throughout Stages 2T and 3T).

In an alternative pathway, the (±)-cis-β-lactam is crystallized from the isomeric mixture (e.g., using ethyl acetate) and the silyl moiety is removed from the C(3) hydroxy group of the N-unsubstituted β-lactam in Stage 3. Generally, methods are known for removing a silyl protecting group. The resulting N-unsubstituted (±)-cis-β-lactam (9) (i.e., (±)-cis-3-hydroxy-4-phenylazetidin-2-one) is then derivatized and optionally resolved according to various pathways to produce appropriate β-lactam side chain precursors for use in the present invention.

Similar to Stage 2T described above, in Stage 4T the N-unsubstituted (±) cis-β-lactam is derivatized by introducing a hydroxy protecting group ($X_6$) to protect the C(3) hydroxy group on the β-lactam. Appropriate hydroxy protecting groups are described in detail above.

The derivatization in Stage 4T also includes introducing a tert-butoxycarbonyl (t-Boc) group (e.g., using di-tert-butyldicarbonate) to the —NH moiety of the N-unsubstituted (±)-cis-β-lactam (9). In various embodiments, the β-lactam side chain precursor utilized in the process of the present invention is the N-t-Boc-3-hydroxy protected β-lactam produced in Stage 4T prior to resolution. Thus, the β-lactam side chain precursor corresponds to (±)-cis-β-lactam (300T) (i.e., the β-lactam is present as a mixture of enantiomers). As noted above, however, in other embodiments it may be desirable to resolve the enantiomeric mixture of N-unsubstituted (±)-cis-β-lactam (9) into its enantiomers. If desired, the resolution in Stage 4T may be performed by various methods known in the art such as, for example, enzymatic resolution, to form optically active (3R,4S)-cis-β-lactam (300T), wherein $X_6$ is a hydroxy protecting group as defined above.

In yet another pathway, N-unsubstituted (±)-cis-β-lactam (9) is resolved by treating the enantiomeric mixture with an N-substituted-L-proline acylating agent (11) in the presence of an amine. Exemplary L-proline acylating agents are acid chlorides, acid anhydrides, or mixed anhydrides of N-t-butoxycarbonyl-L-proline or N-carbobenzyloxy-L-proline (e.g., R″ is t-butoxycarbonyl or carbobenzyloxy and $R^c$ is Cl, $OC(O)R_a$ where $R_a$ is hydrocarbyl, substituted hydrocarbyl or heterocyclo), as shown in Stage 4. When $R^c$ is hydroxy, the optically active proline acylating agent can be prepared by treating the proline acid with an acid acylating agent such as p-toluenesulfonyl chloride (TsCl), methanesulfonyl chloride (MsCl), oxalic acid chloride, di-tert-butyldicarbonate ($Boc_2O$), dicyclohexylcarbodiimide (DCC), alkyl chloroformate, 2-chloro-1,3,5-trinitrobenzene, polyphosphate ester, chlorosulfonyl isocyanate, $Ph_3P$—$CCl_4$, and the like. In one embodiment of this process, the L-proline acylating agent preferentially reacts with one member of the enantiomeric pair to form a C(3) diastereomer (110) from one of the N-unsubstituted β-lactam enantiomers. Thus, the enantiomeric mixture of (±)-cis-β-lactam (9) can be optically enriched in one of the enantiomers by (i) treating the original mixture with L-proline acylating agent to preferentially convert one of the β-lactam enantiomers to an ester derivative (shown in Stage 4) and (ii) selectively recovering the unreacted enantiomer from the ester derivative via crystallization (shown in Stage 5) using, e.g., ethyl acetate, resulting in the optically active 3R,4S (+) cis-β-lactam (9). Alternatively, in another embodiment, the L-proline acylating agent reacts with both enantiomers to produce a pair of diastereomers (110 and 110A). Because these diastereomers have different chemical and physical properties, they can be crystallized under different conditions and thus separated, and the C(3) ester may be hydrolyzed to form the C(3) hydroxy optically active 3R,4S (+) cis-β-lactam (9).

Once the enantiomers are separated, the optically active (3R,4S)-cis-β-lactam (9) is derivatized as described above. As shown in Stage 6, the derivatization includes introducing a hydroxy protecting group ($X_6$) to the C(3) hydroxy group of (3R,4S)-cis-β-lactam (9), resulting in (3R,4S)-cis-β-lactam (90), wherein $X_6$ is a hydroxy protecting group as defined above. Preferably, the C(3) hydroxy group is protected by MOP by treatment with p-toluenesulfonic acid (TsOH) and 2-methoxy-2-propene.

The derivatization also includes derivatizing the —NH moiety of optically active (3R,4S)-cis-β-lactam (90). As shown in Stage 7T, the —NH moiety of (3R,4S)-cis-β-lactam (90) is derivatized by introducing a tert-butoxycarbonyl (t-Boc) group (e.g., using di-tert-butyldicarbonate) to form optically active (3R,4S)-cis-β-lactam (300T) (i.e., (3R,4S)—cis)-N-t-Boc-3-protected hydroxy-4-phenylazetidin-2-one).

One embodiment of the process of the present invention is illustrated in Reaction Scheme 2 (which describes the preparation of docetaxel) wherein $G_1$, $G_2$, $G_3$, $G_4$, $L_1$, $L_2$, and Z are as defined in connection with Formula (2), and $X_6$ is a hydroxy protecting group. Appropriate hydroxy protecting groups are described in detail above.

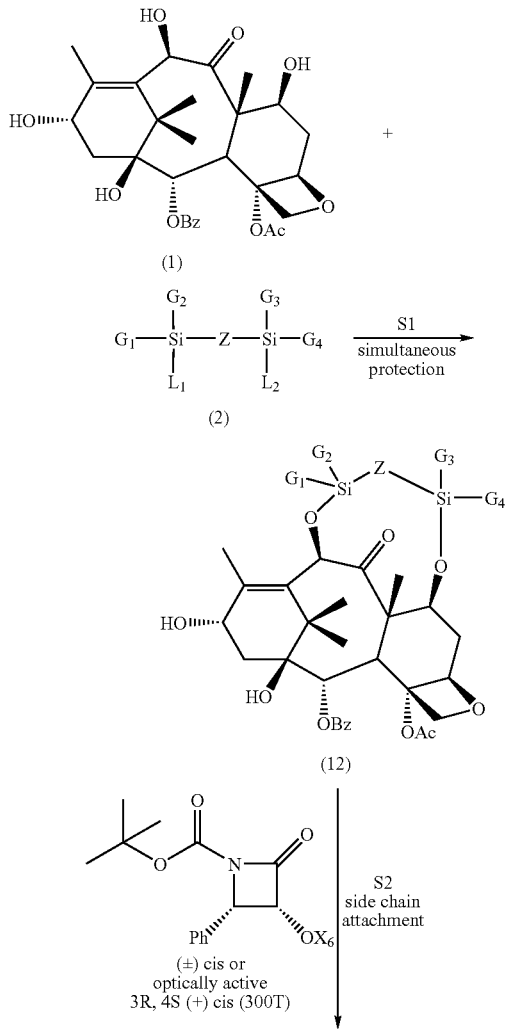

Reaction Scheme 2

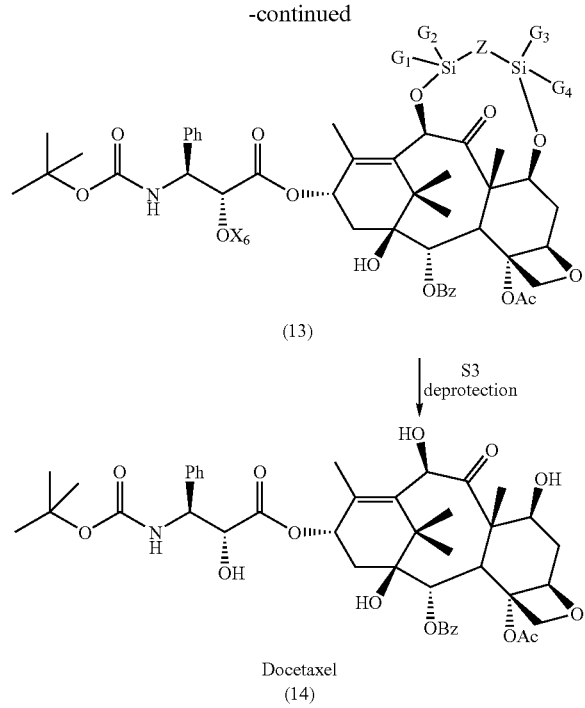

(13)

↓ S3 deprotection

Docetaxel
(14)

Stage 1 of Reaction Scheme 2 illustrates the simultaneous protection of the C(7) and the C(10) hydroxy groups of 10-DAB (1) with a bridging silicon-based protecting group (2) to form 7,10-protected 10-DAB derivative (12). Any bridging silicon-based protecting group described herein may be utilized in this stage. For example, in one embodiment, $G_1$, $G_2$, $G_3$, and $G_4$ are independently substituted or unsubstituted alkyl, alkenyl, alkynyl, aryl, heteroaryl, or cycloalkyl; Z is —$(CH_2)_y$—; and y is a positive integer from 1 to about 8. In another embodiment, $G_1$, $G_2$, $G_3$, and $G_4$ are independently substituted or unsubstituted alkyl, alkenyl, alkynyl, aryl, heteroaryl, or cycloalkyl; Z is —[O—Si($Z_{10}$)($Z_{11}$)-]$_n$O— or —O—; n is 1 or 2; and $Z_{10}$ and $Z_{11}$ are alkyl. In either of these two embodiments, $L_1$ and $L_2$ are independently amine, halide, or sulfonate leaving groups.

The simultaneous protection of 10-DAB (1) is preferably carried out in the presence of a base and a solvent. Appropriate bases include, for example, amine bases such as N,N-4-dimethylaminopyridine (DMAP), and suitable solvents include, for example, polar aprotic solvents such as tetrahydrofuran (THF). Alternatively, however, in other embodiments other bases and solvents, such as inorganic bases and/or non-polar solvents, for example, may be preferred.

In Stage 2, 10-DAB derivative (12) is derivatized by treating derivative (12) with a β-lactam side chain precursor to form 10-DAB derivative (13). As shown, the β-lactam side chain precursor corresponds to (±) cis or optically active 3R,4S (+) cis-β-lactam (300T) (i.e., N-benzoyl-3-protected hydroxy-4-phenylazetidin-2-one), wherein $X_6$ is a hydroxy protecting group as defined above. (±) cis or optically active 3R,4S (+) cis-β-lactam (300T) may be formed by any of the various methods and pathways described above in Reaction Scheme 1, or by other methods known to those of skill in the art.

10-DAB derivative (12) is typically treated with the β-lactam side chain precursor in Stage 2 in the presence of a deprotonating agent (such as an organometallic compound (e.g., n-butyllithium or n-hexyllithium) or a disilazide (e.g., NaHMDS or LHMDS) or an amine or ammonium-containing compound (such as a tetraalkylammonium halide or an alkali metal dialkyl amine). Alternatively, however, 10-DAB derivative (12) may be treated with the β-lactam side chain precursor in the presence of a tertiary amine (such as triethyl amine, diisopropylamine, pyridine, N-methyl imidazole, and N,N-4-dimethylaminopyridine (DMAP)).

Following the formation of 7-protected-10-acetoxy 10-DAB derivative (13), 10-DAB derivative (13) is deprotected to form docetaxel (14) in Stage 3. The various protecting groups are generally removed by hydrolysis (i.e., using a hydrolyzing agent) under relatively mild conditions so as not to disturb the C(13) ester linkage and/or other hydrolyzable substituents on the polycyclic portion of 10-DAB derivative (13) and/or the side chain.

A preferred embodiment of the process of the present invention is illustrated in Reaction Scheme 3 (which describes the preparation of docetaxel) wherein $G_1$, $G_2$, $G_3$, $G_4$, $L_1$, $L_2$, and Z are as defined in connection with Formula (2), and $X_6$ is a hydroxy protecting group as defined above.

Reaction Scheme 3

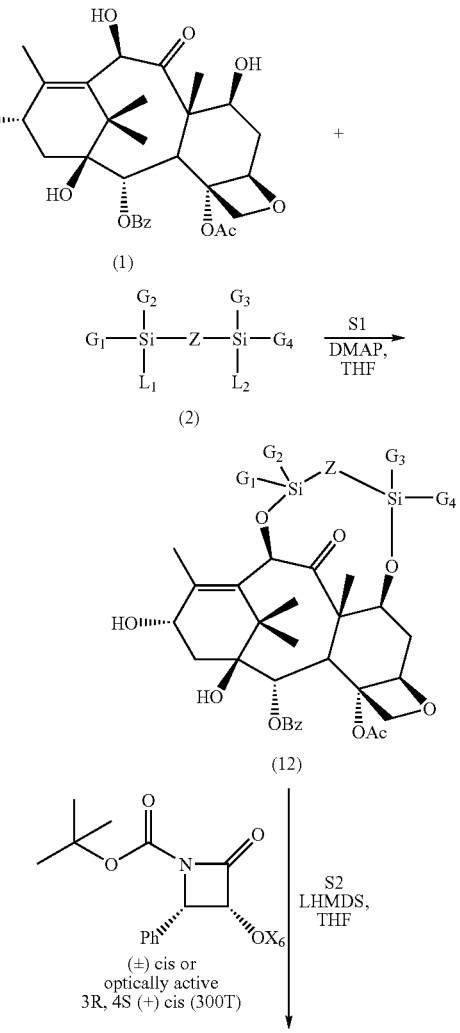

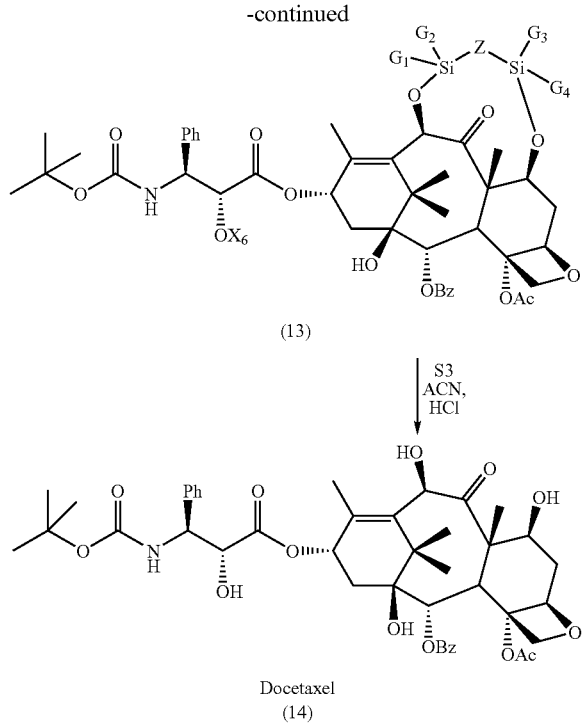

Docetaxel
(14)

Stage 1 of Reaction Scheme 3 illustrates the simultaneous protection of the C(7) and the C(10) hydroxy groups of 10-DAB (1) with a bridging silicon-based protecting group (2) to form 7,10-protected 10-DAB derivative (12). Any bridging silicon-based protecting group described herein may be utilized in this stage. For example, the bridging silicon-based protecting group may be 1,3-dichloro-1,1,3,3-tetramethyldisiloxane (i.e., Formula (2) wherein $L_1$ and $L_2$ are chloro; $G_1$, $G_2$, $G_3$, and $G_4$ are each methyl; Z is —O—). By way of another example, the bridging silicon-based protecting group may be 1,2-bis(chlorodimethylsilyl)ethane (i.e., Formula (2) wherein $L_1$ and $L_2$ are chloro; $G_1$, $G_2$, $G_3$, and $G_4$ are each methyl; Z is —$(CH_2)_y$—; and y is 2). By way of another example, the bridging silicon-based protecting group may be 1,5-dichlorohexamethyltrisiloxane (i.e., Formula (2) wherein $L_1$ and $L_2$ are chloro; $G_1$, $G_2$, $G_3$, and $G_4$ are each methyl; Z is —[O—Si($Z_{10}$)($Z_{11}$)-]$_n$O—; n is 1 and $Z_{10}$ and $Z_{11}$ are methyl). The transformation of 10-DAB (1) to 7,10-protected 10-DAB derivative (12) is accomplished in the presence of N,N-4-dimethylaminopyridine (DMAP) and tetrahydrofuran (THF) solvent.

In Stage 2, 10-DAB derivative (12) is treated with (±) cis or optically active 3R, 4S (+) cis-β-lactam (300T) in the presence of LHMDS and THF to form 7,10 -protected 10-DAB derivative (13). Alternatively, 10-DAB derivative (12) may be treated with (±) cis or optically active 3R,4S (+) cis-β-lactam (300T) in the presence of another deprotonating agent (such as an organometallic compound (e.g., n-butyllithium or n-hexyllithium) or another disilazide (e.g., NaHMDS) or an amine or ammonium-containing compound (such as a tetraalkylammonium halide or an alkali metal dialkyl amine). As noted above, (±) cis or optically active 3R,4S (+) cis-β-lactam (300T) may be prepared according to the various methods described in Reaction Scheme 1, or by other methods known to those of skill in the art.

Following the formation of 7-protected-10-acetoxy 10-DAB derivative (13), 10-DAB derivative (13) is treated with hydrochloric acid (HCl) in the presence of acetonitrile (ACN) to remove (i.e., deprotect) the C(7), C(10), and C(2') hydroxy protecting groups, thus forming docetaxel (14).

Abbreviations And Definitions

The following definitions and methods are provided to better define the present invention and to guide those of ordinary skill in the art in the practice of the present invention. Unless otherwise noted, terms are to be understood according to conventional usage by those of ordinary skill in the relevant art.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, keto, acyl, acyloxy, nitro, amino, amido, nitro, cyano, thiol, ketals, acetals, esters, ethers, and thioethers.

The term "heteroatom" shall mean atoms other than carbon and hydrogen.

Unless otherwise indicated, the alkyl groups described herein are preferably lower alkyl containing from one to eight carbon atoms in the principal chain and up to 20 carbon atoms. They may be straight or branched chain or cyclic and include methyl, ethyl, propyl, isopropyl, butyl, hexyl, and the like.

Unless otherwise indicated, the alkenyl groups described herein are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halide," "halogen" or "halo" as used herein alone or as part of another group refer to chlorine, bromine, fluorine, and iodine.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics such as furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The term "heteroaromatic" as used herein alone or as part of another group denote optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The term "acyl," as used herein alone or as part of another group, denotes the moiety formed by removal of the hydroxy group from the group —COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl or substituted hydrocarbyl.

The term "acyloxy," as used herein alone or as part of another group, denotes an acyl group as described above bonded through an oxygen linkage (—O—), e.g., RC(O)O— wherein R is as defined in connection with the term "acyl."

Unless otherwise indicated, the alkoxycarbonyloxy moieties described herein comprise lower hydrocarbon or substituted hydrocarbon or substituted hydrocarbon moieties.

The terms "hydroxy protecting group" as used herein denote a group capable of protecting a free hydroxy group ("protected hydroxy") which, subsequent to the reaction for which protection is employed, may be removed without disturbing the remainder of the molecule. Exemplary hydroxy protecting groups include ethers (e.g., allyl, triphenylmethyl (trityl or Tr), benzyl, p-methoxybenzyl (PMB), p-methoxyphenyl (PMP)), acetals (e.g., methoxymethyl (MOM), β-methoxyethoxymethyl (MEM), tetrahydropyranyl (THP), ethoxy ethyl (EE), methylthiomethyl (MTM), 2-methoxy-2-propyl (MOP), 2-trimethylsilylethoxymethyl (SEM)), esters (e.g., benzoate (Bz), allyl carbonate, 2,2,2-trichloroethyl carbonate (Troc), 2-trimethylsilylethyl carbonate), silyl ethers (e.g., trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS) and the like. A variety of protecting groups for the hydroxy group and the synthesis thereof may be found in "Protective Groups in Organic Synthesis" by T. W. Greene and P. G. M. Wuts, John Wiley & Sons, 1999.

As used herein, "10-DAB" means 10-deacetylbaccatin III; "Ac" means acetyl (i.e., $CH_3C(O)$—); "ACN" means acetonitrile; "Bz" means benzoyl (i.e., $C_6H_5C(O)$—); "$Boc_2O$" means di-tert-butyldicarbonate; "Cbz" means carbobenzyloxy; "DMAP" means N,N-4-dimethylaminopyridine; "EtOAc" means ethyl acetate; "LHMDS" means lithium hexamethyldisilazide; "MsCl" means methanesulfonyl chloride; "NaHMDS" means sodium hexamethyldisilazide; "nBuLi" means n-butyllithium; "Ph" means phenyl; "t-Boc" means tert-butoxycarbonyl; "TEA" means triethylamine; "THF" means tetrahydrofuran; "TMSCl" means trimethylsilyl chloride; and "TsOH" means p-toluenesulfonic acid.

The term "taxane" as used herein, denotes compounds containing the A, B and C rings (with numbering of the ring positions shown herein):

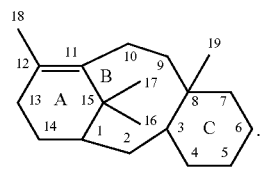

The following examples illustrate the invention.

EXAMPLE 1

Preparation of Trimethylsilyl 2-(Trimethylsilyloxy)Acetate

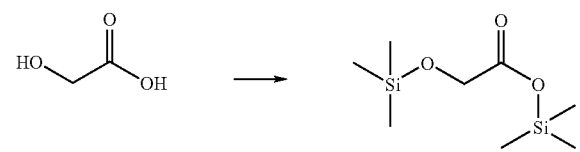

Trimethylsilyl 2-(trimethylsilyloxy)acetate is available from many vendors. However, it can be easily prepared from inexpensive glycolic acid ($75/Kg from Aldrich) and trimethylsilyl chloride ($80/Kg from Aldrich) in the presence of 2 equivalents of pyridine. Typically, glycolic acid (76.05 g, 1 mol) was dissolved in dry pyridine (164 mL, 2 mol) then the mixture was cooled to 0 to 5° C. in an ice-water bath with stirring. Neat trimethylsilyl chloride (108.64 g, 1 mol) was added drop-wise to control the exotherm to less than 40° C. Pyridinium chloride precipitated as a free flowing solid. Heptane (500 mL) was added to aid the agitation. The second equivalent of neat trimethylsilyl chloride was added and the mixture was stirred at ambient 22 to 40° C. for 30 minutes until the reaction was complete. The mixture was further diluted with heptane (1 L) and the salt was allowed to precipitate out. The heptane layer was siphoned into the rotary evaporator through a medium porous inline filter and concentrated to give a clear oil (215 g, 0.98 mol) of the trimethylsilyl 2-(trimethylsilyloxy)acetate. It was distilled in the rotary evaporator at 70 to 75° C. under vacuum of 6 to 8 mmHg.

EXAMPLE 1A

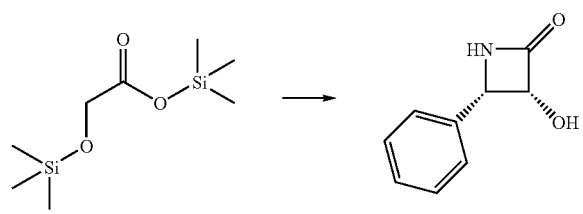

When the reaction of the lithium enolate (made by treating trimethylsilyl-(trimethylsilyloxy)acetate with lithium hexamethyldisilazide) with trimethylsilylbenzaldimine (generated in situ from aldehyde (1a-f below) and lithium hexamethyldisilazide) reported by Hart et al. (*Chem. Rev.* 1989, 89, 1447-1465) was examined, the enolate decomposition occurred faster than its reaction with the imine at 0 to 5° C. A solution to this problem was found by lowering the temperature of the enolate's reaction to −25° C. and using an excess (e.g., 2 eqs) amount of the enolate.

Thus, benzaldehyde (5.3 g, 0.05 mol) was added to the 1.0 M solution of LHMDS in THF (150 mL 0.15 mol) at 0° C. and the mixture was stirred for 30 minutes before cooling to −30 to −25° C. Once the reaction temperature was at −30° C., a 1 M solution of the trimethylsilyl 2-(trimethylsiloxy)acetate ester (22.0 g, 0.1 mol, 2 eq) in THF was added drop-wise to control the exotherm to maintain the reaction temperature to <−25° C. The mixture was stirred at this temperature for 1 h before warming to −5 to 0° C. The mixture was stirred at this temperature for 18 h. The mixture was quenched with a saturated solution of sodium bicarbonate (100 mL) and extracted with 1-butanol (500 mL). The 1-butanol was evaporated under vacuum and the residue was taken up in methanol (75 mL) and sodium carbonate (0.5 g, 0.005 mol) for approximately 1 h at ambient temperature. The reaction mixture then was quenched with acetic acid (0.6 g, 0.010 mol), triethylamine (2 g, 0.02 mol), and diluted with 100 mL of ethyl acetate. The mixture was filtered through a pad of silica gel (50 g) and the filtrate was concentrated on a rotary evaporator at 40° C. until crystal formation occurred. The mixture was cooled in a 0° C. ice bath for 30 min and the crystals were collected via vacuum filtration, washed with cold ethyl acetate, and dried to a constant weight of 4.13 g (50% yield); a white powder resulted.

EXAMPLE 2

Preparation of 3-Hydroxy-4-Substituted-Azetidin-2-Ones

A 1 M solution of LHMDS in THF (100 mL, 0.1 mol) was cooled to 0° C. and a 1 M solution of trimethylsilyl 2-(trimethylsilyloxy)acetate (22.0 g, 0.1 mol) in THF that was prepared as in Example 1 was added drop-wise to control the exotherm and maintain the temperature at 0° C. to 5° C. To this solution was added 1 equivalent of trimethylsilyl chloride followed by the addition of 1 equivalent of LHMDS and 1 equivalent of benzaldehyde with stirring at 0 to 15° C. over 14 h. The 3-trimethylsilyloxy β-lactam products were observed (via HNMR of reaction mixture) as a 5:1 cis:trans ratio in quantitative yield. This process is depicted in Scheme 4 below.

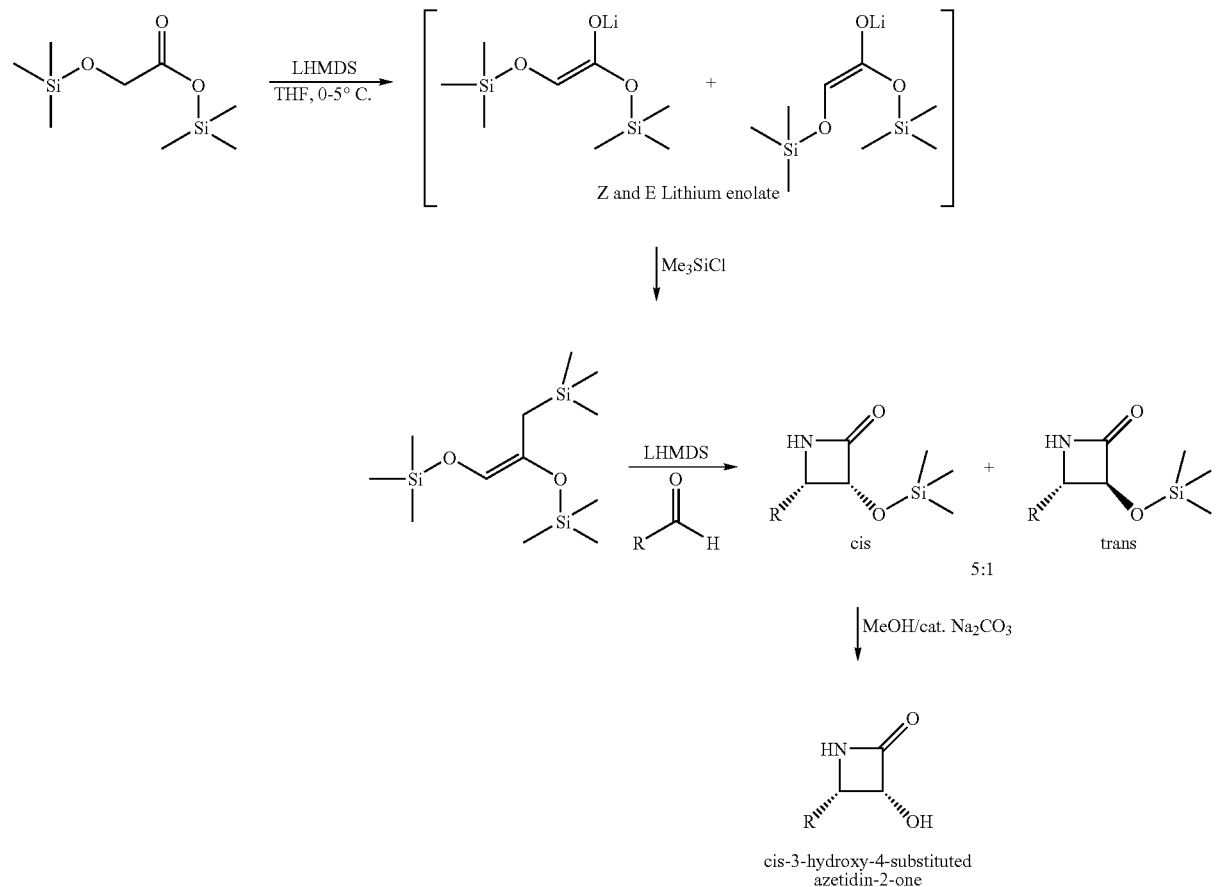

Methanolysis of the silyl ether was easily accomplished in 15 minutes at ambient temperature with a catalytic amount of sodium carbonate and the desired product cis-hydroxy-4-substituted-β-lactam crystallized out in 48% isolated yield upon concentration from ethyl acetate.

EXAMPLE 3

Preparation of 3-Hydroxy-4-Thienyl-Azetidin-2-One

Typically, a 1.0 M THF solution of lithium hexamethyldisilazide (140 mL, 0.14 mol) under nitrogen was diluted with THF (140 mL) and cooled to 0 to 5° C. with an ice-water bath. The trimethylsilyl 2-(trimethylsilyloxy)acetate (33.4 g, 0.14 mol) was added drop-wise over 20 minutes. To this enolate solution was added trimethylsilylchloride (17.7 mL, 0.14 mol) and after 5 minutes of stirring, a second portion of LHMDS solution in THF (100 mL, 0.10 mol) was added over 10 minutes. To this solution was added 2-thiophenecarboxaldehyde (11.2 g, 0.1 mol) drop-wise over 15 to 20 min to control the exotherm at <5° C. This solution was stirred at 0 to 5° C. over 14 h corresponding to complete disappearance of the imine.

The reaction was neutralized with glacial acetic acid (6 g, 0.10 mol) and diluted with ethyl acetate (400 mL) and transferred to a 2-L separatory funnel. The mixture was washed with water (100 mL) and brine (100 mL). The organic layer was dried over sodium sulfate, filtered through a pad of silica gel and concentrated to give a yellow solid. The solid was taken up in methanol (300 mL) and solid $Na_2CO_3$ (1.0 g) and the mixture was stirred at ambient temperature for 15 min. TLC monitoring eluting with 2:1 ethyl acetate:hexanes showed complete conversion from the non-polar TMS-ether (Rf=0.7) to the polar product (Rf=0.25). The reaction was quenched with glacial acetic acid (0.6 mL) and the mixture was concentrated to a solid. The solid was dissolved in hot ethyl acetate (500 mL) and the insoluble salts were filtered off through a pad of silica gel. The filtrate was concentrated under rotary evaporation at 40° C. to approximately 40 mL of volume to induce crystal formation. The mixture was cooled to ambient temperature and the crystals (8.13 g, 0.048 mol, 48% yield) were collected as a white powder. Furthermore, the process was conveniently carried out in a one-pot operation when the reaction was quenched with sodium bicarbonate and extracted with 1-butanol and ethyl acetate as described in Example 4.

EXAMPLE 4

Preparation of Various Azetidin-2-Ones

The ketene acetal tris(trimethylsilyloxy)ethene is a commercially available product, and can be used for the synthesis of β-lactams starting from various aldehydes as depicted in Scheme 7 below. Thus, when benzaldehyde was treated with a THF solution of lithium hexamethyldisilazide at 0° C., the N-trimethylsilylbenzaldimine was generated instantaneously along with an equivalent of lithium trimethylsilanolate. Stirring this mixture with the ketene acetal at 10 to 15° C. for 14 h resulted in the formation of the β-lactams similar to the reaction in Scheme 5. This ketene acetal reaction was found to be general across various aromatic and enolizable aliphatics we examined (see Table 2) and produced predominantly cis-β-lactams in all cases.

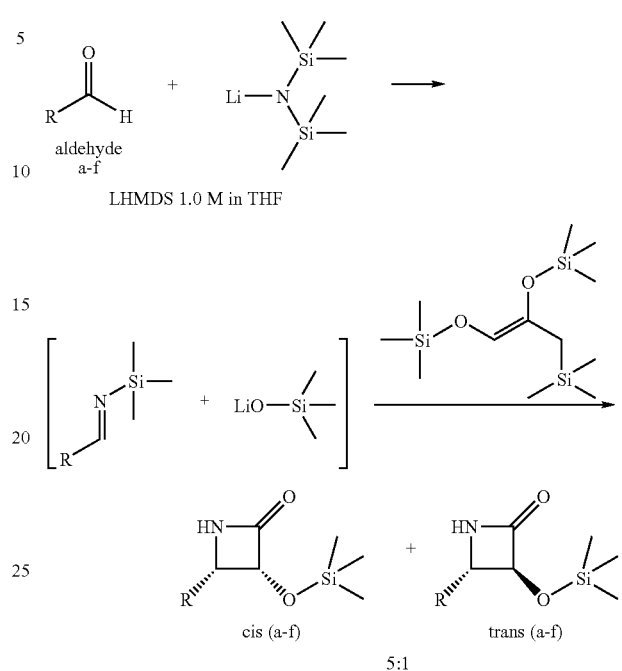

Scheme 5

TABLE 2

| | Aldehyde | Cis:trans |
|---|---|---|
| a | ![benzaldehyde] | 5:1 |
| b | ![cyclopropanecarboxaldehyde] | 3:1 |
| c | ![furfural] | 5:1 |
| d | ![2-thiophenecarboxaldehyde] | 5:1 |
| e | ![2-pyridinecarboxaldehyde] | 4:1 |

TABLE 2-continued

| | Aldehyde | Cis:trans |
|---|---|---|
| f | (cyclopentanecarboxaldehyde structure) | 3:1 |

To optimize the reaction conditions, 0.8 equivalents of trimethylsilylchloride were added prior to the addition of the ketene acetal. This modification resulted in an increase in isolated yield to 66% of the product β-lactam a (Scheme 6). Thus, in a single operation starting with the readily available benzaldehyde and tris(trimethylsilyloxy)ethene we obtained β-lactam a in high purity which is an important intermediate for the synthesis of taxanes.

Scheme 6

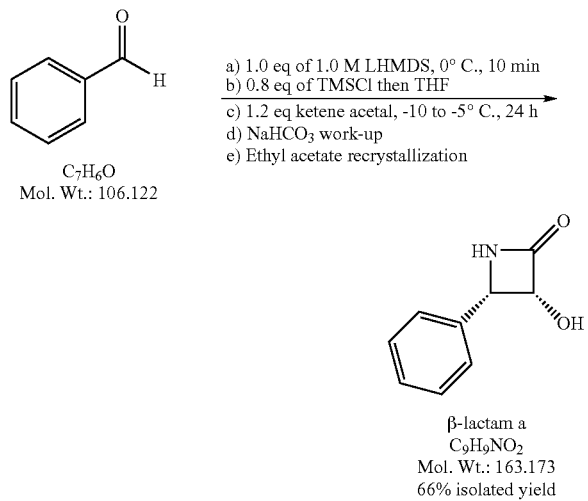

a) 1.0 eq of 1.0 M LHMDS, 0° C., 10 min
b) 0.8 eq of TMSCl then THF
c) 1.2 eq ketene acetal, -10 to -5° C., 24 h
d) NaHCO₃ work-up
e) Ethyl acetate recrystallization $C_7H_6O$
Mol. Wt.: 106.122

β-lactam a
$C_9H_9NO_2$
Mol. Wt.: 163.173
66% isolated yield

In one experiment, a 0.5 M solution of LHMDS in THF was cooled to −10 to 0° C. then 1.0 equivalent of benzaldehyde was added over 15 min to control the exothermic imine reaction temperature to <15° C. Once the reaction temperature was −10 to −5° C., neat tris(trimethylsilyl)ethene (1.2 eq) was added. The mixture was stirred at this temperature over 14 h. Reaction completion was monitored by HNMR for the disappearance of the imine. Once complete, trimethylsilyl chloride (1 eq) was added to convert the lithium trimethylsilanolate to the volatile hexamethyldisiloxane. The reaction was washed twice with water at 1/10 the volume of reaction mixture to remove the lithium chloride salt. To the THF solution was added a catalytic amount of 1.0 M HCl and stirred for 2 h for complete desilylation the intermediate (Rf=0.8) as monitored by TLC analysis (EtOAc:Heptane, 3:1) to give the product (Rf=0.2). The hydrochloric acid in the reaction was quenched with triethylamine and the mixture was filtered through a pad of silica gel followed by exchange of the THF with ethyl acetate under rotary evaporation. The crystals were collected as a white solid and washed with cold ethyl acetate. β-lactam a: mp: 140 to 145° C.; ¹H NMR (400 MHz, CDCl₃) (ppm): 2.26 (d, J=9.4 Hz, 1H), 4.96 (d, J=4.96 Hz, 1H, 5.12 (m, 1H), 4.15 (bm, 1H), 7.41 (m, 5H).

In another experiment, benzaldehyde was added to a 1.0 M THF solution of LHMDS (100 mL, 0.1 mol) at 0° C. and the mixture was stirred for 15 minutes followed by the addition of TMSCl (10 mL, 0.08 mol). To this solution was added tris (trimethylsilyloxy)ethylene (40 mL, 0.12 mol) and the mixture was stirred at −10 to −5° C. over 24 h. The mixture was warmed to ambient temperature over 2 h and quenched with saturated sodium bicarbonate (25 mL) and stirred at ambient temperature for 30 min and the layers were separated. The aqueous layer was back extracted with 1-butanol (200 mL) and the organic layers were combined and washed with brine (50 mL), dried over sodium sulfate, filtered through a pad of silica gel and concentrated to give a solid. The solid was taken up in hot ethyl acetate (800 mL) and the insoluble solids were filtered off through a pad of silica gel. The filtrate was concentrated under rotary evaporation at 40° C. to approximately 15 mL in volume to induce crystal formation. The mixture was cooled to ambient temperature and the crystals (10.73 g, 0.025 mol, 66% yield) were collected as a white powder. β-lactam a: mp: 140 to 145° C.; ¹H NMR (400 MHz, CDCl₃) (ppm): 2.26 (d, J=9.4 Hz, 1H), 4.96 (d, J=4.96 Hz, 1H, 5.12 (m, 1H), 4.15 (bm, 1H), 7.41 (m, 5H).

EXAMPLE 5

Trimethylsilyl 2-(Trimethylsilyoxy)Acetate

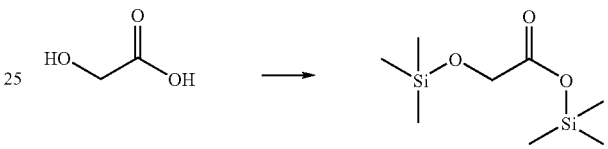

Glycolic acid (91.2 g, 2.4 mol) was dissolved in pyridine (194 g, 2.45 mol) and acetonitrile (600 mL) by mechanical stirring under nitrogen and reflux condensor. Trimethylsilylchloride (TMSCl, 260 g, 2.4 mol) was added via an addition funnel over 30 min. The mixture was stirred for 30 min and the hexanes (250 mL) was added and the phases were separated. To the bottom layer was added a second lot of hexanes (100 mL) and agitated vigorously for 5 minutes. Then the phases were separated and the hexanes layers were combined and concentrated under rotary evaporation at 30° C. to give 240 g (91% yield) of the known acetate.

EXAMPLE 6

Tris(Trimethylsiloxy)Ethane

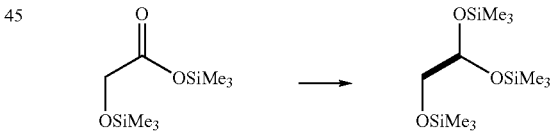

To a 0.5 M THF solution of LHMDS (200 mL, 0.1 mol) at 0° C. was added the trimethylsilyl-2-(trimethylsiloxy)acetate (23.9 mL, 0.1 mol) drop-wise over 15 minute and the mixture was stirred at this temperature for an additional 15 min to generate the lithium enolate. Trimethylsilyl chloride (12.5 mL, 0.1 mol) was added over 15 minutes to trap the enolate as the tris(trimethylsiloxy)ethene product. The mixture was warmed to ambient temperature and the THF solvent was removed by vacuum rotary evaporation at 40° C. to precipitate out the lithium chloride. The mixture was taken up in 300 mL of hexanes and 5 mL of triethylamine and stirred for 5 min; the salt was allowed to settle. The supernatant was filtered through a pad of diatomaceous earth twice to give a clear solution. The solution was concentrated under rotary evaporation to give the lightly yellow colored oil product. The solution was concentrated under rotary evaporation to give the lightly yellow colored oil product identical to the commercial product. Bp=90° C. at 1 mmHg.

EXAMPLE 7

N-Trimethylsilyl-3-Trimethylsiloxy-4-Phenyl-Azetidin-2-One

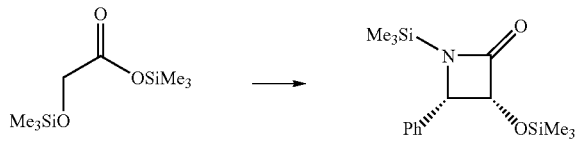

A one-pot procedure for the synthesis of previously unreported N-trimethylsilyl beta-lactam from the trimethylsilyl-2-trimethylsiloxy-acetate has been discovered to be an efficient economical method not requiring cryogenic cooling. To a magnetically stirring solution of hexamethyldisilazane (390 g, 2.42 mol) in dry 1,2-dimethoxyethane (505 mL) under nitrogen with a circulation chiller at 0° C. was added a 2.5 M solution of n-butyllithium (840 mL, 2.1 mol) at a rate so as to control the exothermic reaction temperature to <30° C. (over 45 min) to generate the required LHMDS base in situ. Once the LHMDS solution temperature has reached <10° C., a neat mixture of TMSCl (119.5 g, 1.1 mol) and the trimethylsilyl-2-(trimethylsiloxy)acetate (240 g, 1.1 mol) was added over 15 minutes to give the tris(trimethylsiloxy)ethene in situ. Then neat benzaldehyde (106.12 g, 1.0 mol) was added at a rate so as to control the exothermic reaction temperature to <25° C. to give the N-trimethylsilyl-benzaldimine in situ. The mixture was allowed to react at ambient temperature (22° C.) until $^1$HNMR monitoring indicated that the disappearance of the ketene acetal resonance at 5.4 ppm (CDCl$_3$) occurred at 12 h of reaction time. The reaction mixture was quenched with trimethylchlorosilane (TMSCl, 108.64 g, 1.0 mol), triethylamine (25.3 g, 0.25 mol) followed by acetic acid (6.0 g, 0.1 mol) while keeping the exothermic reaction temperature to <22° C. The mixture was diluted with hexanes (500 mL) and the resulting lithium chloride salt was filtered off through a pad of celite (200 g) followed by filter cake washing with hexanes (250 mL). The filtrate was concentrated under rotary vacuum evaporation to a residue. The residue was taken up in hexanes (500 mL) and allowed to stand at −25° C. to induce crystal formation. The white crystals were collected by vacuum filtration, washed with cold −20° C. hexanes (200 mL), and dried to a constant weight of 152 g. The filtrate was concentrated to a residue, taken up in hexanes (200 mL), and recrystallized as previous to give a second crop of 32 g. The crops were combined (184 g, 60% yield) after HNMR analysis to be pure cis-N-trimethylsilyl-3-trimethylsiloxy-4-phenyl-azetidin-2-one. Mp: 53 to 55° C. $^1$H NMR (400 MHz, CDCl$_3$) δ (ppm): 0.11 (s, 9H), 0.14 (s, 9H), 4.63 (d, J=5.01 Hz, 1H), 5.06 (d, J=5.01 Hz, 1H), 7.31 (m, 5H).

EXAMPLE 8

Cis-3-Trimethylsiloxy-4-Phenyl-Azetidin-2-One

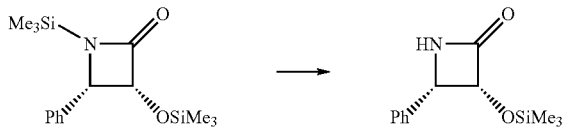

To a solution of N-trimethylsilyl-3-trimethylsiloxy-4-phenyl-azetidin-2-one (140 g, 0.46 mol) in hexanes (600 mL) at ambient temperature was added triethylamine (101 g, 1 mol), methanol (22 g, 0.7 mol) and the mixture was stirred for 15 minutes resulting in crystal formation of the N-desilylated product. The mixture was cooled to 0° C. for 15 min and the white crystals were collected by vacuum filtration, washed with cold hexanes, and dried to a constant weight of 94 g (87% yield). Mp: 118 to 120° C., $^1$H NMR (400 MHz, CDCl$_3$) δ (ppm): −0.08 (s, 9H), 4.79 (d, J=4.4 Hz, 1H), 5.09 (dd, J=4.4, 2.7 Hz, 1H), 6.16 (bm, 1H), 7.3 to 7.4 (m, 5H).

EXAMPLE 9

Cis-3-Hydroxy-4-Phenyl-Azetidin-2-One

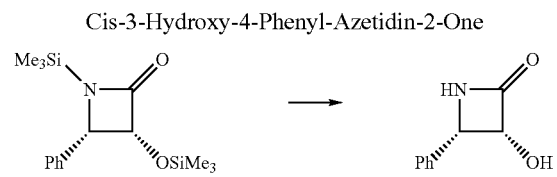

To a heterogeneous solution of N-trimethylsilyl-3-trimethylsiloxy-4-phenyl-azetidin-2-one (150 g, 0.49 mol) in methanol (500 mL) was added a catalytic amount of trimethylchlorosilane (1.08 g, 1 mmol) and the mixture was stirred at ambient temperature to give a clear solution. Thin layer chromatography (TLC) monitoring of the reaction eluting with ethyl acetate and hexanes (3:1) indicated that complete conversion was achieved after 15 minutes. The reaction mixture was quenched with triethylamine (10.1 g, 0.1 mol) and the methanol was removed under rotary evaporation at 40° C. until crystals formed. Ethyl acetate (300 mL) was added and the evaporation was continued to remove the remaining methanol to give a thick slurry before cooling to 0 to 5° C. for 20 minutes. The white crystals were collected via vacuum filtration following by washing with cold 0° C. ethyl acetate (75 mL) and dried to constant weight of 75 g (94% yield) of the desire product described previously.

EXAMPLE 10

1-(Triethylsilyloxy)-1,2-Bis(Trimethylsilyloxy)Ethane

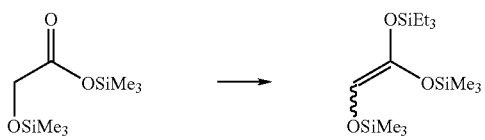

To a solution of diisopropylamine (15.5 mL, 0.11 mol) in THF (100 mL) at −78° C. was added a 1.6 M hexanes solution of n-butyl lithium (70 mL, 0.11 mol) over 15 minutes. After stirring for an additional 15 minutes at this temperature, triethylsilylchloride (16.7 mL, 0.1 mol) was added over 10 minutes followed by the addition of trimethylsilyl-2-(trimethylsiloxy)acetate (24.4 mL, 0.1 mol) over 30 minutes. The reaction was stirred at −78° C. for 30 minutes and warmed to ambient temperature by removing the cryogenic bath. The THF solvent was removed by vacuum rotary evaporation at 40° C. to precipitate out the lithium chloride. The mixture was taken up in 300 mL of hexanes and 5 mL of triethylamine and stirred for 5 min and the salt was allowed to settle. The supernatant was twice filtered through a pad of diatomaceous earth to give clear solution. The solution was concentrated under rotary evaporation to give the lightly yellow colored oil product as a mixture of geometrical isomers (4:1).

EXAMPLE 11

Triethylsilyl-2-(Triethylsilyloxy)Acetate

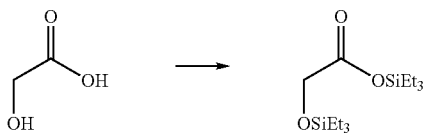

Glycolic acid (76.05 g, 1 mol) was dissolved in dry pyridine (164 mL, 2 mol) and the mixture was cooled to with ice-water bath with stirring. Neat triethylsilyl chloride (115 g, 1 mol) was added drop-wise to control the exotherm to less than 40° C. Pyridinium chloride precipitated as a free flowing solid. Heptane (500 mL) was added to aid the agitation. The second equivalent of neat triethylsilylchloride was added and the mixture was stirred as ambient temperature (22 to 40° C.) for 30 minutes until the reaction was complete. The mixture was further diluted with heptane (1 L) and the salt was allowed to precipitate out. The heptane layer was siphoned into the rotary evaporator through a medium porous inline filter and concentrated to give a clear oil (215 g, 0.98 mol) of the triethylsilyl-2-(triethylsilyloxy)acetate ester. The oil was further purified by vacuum distillation. Bp: 128 to 130° C., 1.5 mmHg. $^1$H NMR (400 MHz, CDCl$_3$) δ (ppm): 0.64 (q, J=8.04 Hz, 6H) 0.78 (q, J=8.04, 6H), 0.97 (t, J=8.04, 2×9H), 4.2 (s, 2H).

EXAMPLE 12

Tris(Triethylsiloxy)Ethane

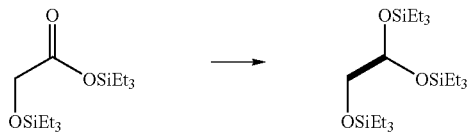

The ester was added to a 0.5 M THF (200 mL, 0.1 mol) solution over 15 minutes and the mixture was stirred at this temperature for an additional 15 minutes to generate the lithium enolate. Triethylsilyl chloride (16.7 mL 0.1 mol) was added over 15 minutes to trap the enolate as the tris(triethylsiloxy)ethene product. The mixture was warmed to ambient temperature and the THF solvent was removed by vacuum rotary evaporation at 40° C. to precipitate out the lithium chloride. The mixture was taken up in 300 mL of hexanes and 5 mL of triethylamine and stirred for 5 minutes while the salt was allowed to settle. The supernatant was twice filtered through a pad of diatomaceous earth to give a clear solution. The solution was concentrated under rotary evaporation to give the lightly yellow colored oil product.

EXAMPLE 13

1,2-Bis(Triethylsilyloxy)-1-(Trimethylsilyloxy) Ethene

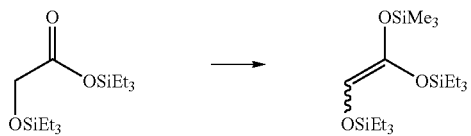

To a solution of diisopropylamine (15.5 mL, 0.11 mol) in THF (100 mL) at −78° C. was added a 1.6 M hexanes solution of n-butyl lithium (70 mL, 0.11 mol) over 15 minutes. After stirring for an additional 15 minutes at this temperature, triethylsilylchloride (16.7 mL, 0.1 mol) was added over 10 minutes followed by the addition of triethylsilyl-2-(triethylsiloxy)acetate (37.6 g, 0.1 mol) over 30 minutes. The reaction was stirred at −78° C. for 30 minutes and warmed to ambient temperature by removing the cryogenic bath and the THF solvent was removed by vacuum rotary evaporation at 40° C. to precipitate the lithium chloride. The mixture was taken up in 300 mL of hexanes and 5 mL of triethylamine and stirred for 5 minutes and the salt was allowed to settle. The supernatant was twice filtered through a pad of diatomaceous earth to give a clear solution. The solution was concentrated under rotary evaporation to give the lightly yellow colored oil product as a 1:1 mixture of geometrical isomers.

EXAMPLE 14

Cis-3-Triethylsiloxy-4-Phenyl-Azetidin-2-One

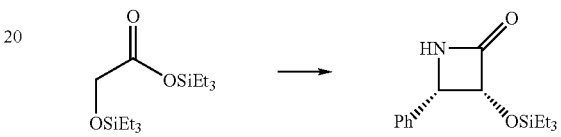

To a magnetically stirring solution of hexamethyldisilazane (39 g, 0.242 mol) in dry 1,2-dimethoxyethane (50 mL) under nitrogen with a circulation chiller at 0° C. was added a 2.5 M solution of n-butyllithium (84.0 mL, 0.21 mol) at a rate so as to control the exothermic reaction temperature to <30° C. (over 15 min) to generate the required LHMDS base in situ. Once the LHMDS solution temperature reached <−30° C., a neat solution of TMSCl (12 g, 0.11 mol) was added and the triethylsilyl-2-(triethylsiloxy)acetate (33.5 g, 0.11 mol) was added over 15 minutes to give the 1,2-bis(triethylsilyloxy)-1-(trimethylsilyloxy)ethene in situ as a mixture of geometrical isomers (6:1). Then, neat benzaldehyde (10.6 g, 0.10 mol) was added at a rate so as to control the exothermic reaction temperature to <−25° C. to give the N-trimethylsilyl-benzaldimine in situ. The hexanes solvent was removed under vacuum and the mixture was allowed to react at ambient temperature (22° C.) until $^1$HNMR monitoring indicated that the disappearance of the ketene acetal resonance at 5.43 ppm (CDCl$_3$) had occurred after 14 h of reaction time. The reaction mixture was quenched with trimethylchlorosilane (TMSCl, 10.8 g, 1.0 mol), triethylamine (2.53 g, 0.025 mol) and acetic acid (0.60 g, 0.01 mol) while keeping the exothermic reaction temperature to <22° C. The mixture was diluted with hexanes (50 mL) and resulting lithium chloride salt was filtered off through a pad of celite (20 g) followed by washing the filter cake with hexanes (25 mL). The filtrate was concentrated under rotary vacuum evaporation to a residue. The residue was taken up in hexanes (50 mL), triethylamine (5 mL) and methanol at ambient temperature and stirred for 15 minutes. TLC analysis of the mixture eluting with ethyl acetate:hexanes (2:1) indicated complete conversion to the desired product (R$_f$=0.45) after 10 minutes of reaction time. The mixture was then diluted with ethyl acetate (100 mL), filtered through a pad of silica gel (25 g) and concentrated until crystals formed. The crystals were collected via vacuum filtration, washed with hexanes and dried to a constant weight of 7.68 g as a white free flowing powder. Upon standing for 2 h at ambient temperature, the filtrate gave 2.8 g of a second crop after harvest. The combined yield was 38%. Mp: 98 to 100° C. $^1$H NMR (400 MHz, CDCl$_3$) δ (ppm): 0.44 (m, 6H), 0.78 (t, J=8.0 Hz, 9H), 4.80 (d, J=4.80, 1H), 5.08 (dd, 4.80, 2.80, 2H), 6.18 (bs, 1H), 7.28 to 7.38 (m, 5H).

EXAMPLE 15

Cis-N-T-Butoxycarbonyl-3-(2-Methoxy-2-Propoxy)-4-Phenyl-Azetidin-2-ONE

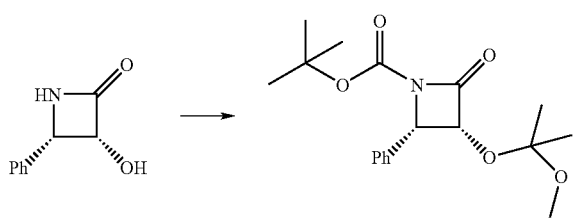

Racemic cis-3-hydroxy-4-phenyl-azetidin-2-one (100 g, 0.61 mol) was dissolved in THF (2.7 L) at ambient temperature at approximately 25 mL/g then cooled to −10 to −15° C. TsOH monohydrate catalyst (3.5 g, 0.018 mol, 3 mol %) was added and then 2-methoxy-2-propene (65 mL, 1.1 to 1.2 eq) was added drop-wise to control the exothermic reaction. The reaction was monitored by TLC and the 2-methoxy-2-propene (2.9 mL) was charged as needed until the disappearance of the starting material was achieved. Triethylamine (85 mL, 0.612 mol) was added to quench the TsOH catalyst. Di-tert-butyldicarbonate (160.5 g, 0.735 mol, 1.2 eq) was added along with DMAP (2.25 g, 0.018 mol, 3 mol %) and the reaction was allowed to proceed at ambient temperature until complete. The mixture was diluted with heptane (1.97 L) approximately equal in volume to the THF used and filtered through a bed of silica gel (100 g) to remove the polar catalysts. The filter cake was washed with 1 L of a 1:1 mixture of ethyl acetate:heptane to ensure complete product recovery. The filtrate was concentrated until crystal formation occurred. Crystals were collected and washed with ice-cold heptane containing 2% triethylamine. The powder was dried to constant weight of 161.0 g (0.48 mol, 78%) under vacuum (0.1 mmHg) at ambient (22° C.) temperature. Mp: 90 to 92° C., $^1$H NMR (400 MHz, CDCl$_3$) δ (ppm): 0.92 (s, 3H), 1.21 (s, 3H), 1.37 (s, 9H), 1.58 (s, 3H), 3.12 (s, 3H), 5.03 (d, J=5.69 Hz, 1H), 5.17 (d, J=5.69 Hz, 1H), 7.33 (m, 5H).

EXAMPLE 16

Racemic Cis-3-Trimethylsilyloxy-4-Phenyl-Azetidin-2-One

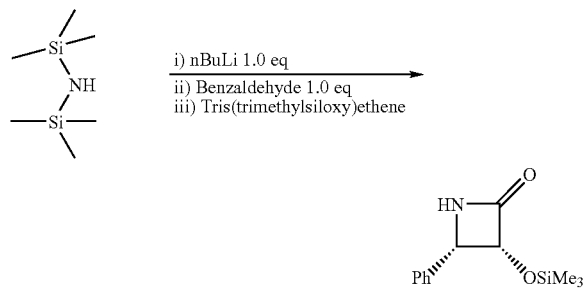

To a solution of hexamethyldisilazane (HMDS, 460 mL, 2.2 mol) in anhydrous dimethoxyethane (200 mL) at 0° C. was added a 2.5 M solution of n-butyllithium (nBuLi, 800 mL, 2.0 mol) over 45 min to maintain the reaction temperature at less than 40° C. After the addition, benzaldehyde was added to the reaction mixture over 1 h to maintain the reaction temperature at less than 40° C. After the addition was complete the mixture was cooled to 0° C. and tris(trimethylsiloxy)ethane (643 g, 2.2 mol) was added and the mixture was stirred until reaction was complete (12 h); reaction completion was determined by the disappearance of the starting ethene material. The reaction mixture was quenched with trimethylsilyl-chloride (TMSCl, 217.28 g, 1.0 eq), triethylamine (50 mL) and acetic acid (20 mL) and diluted with ethyl acetate (1.0 L). The lithium salt was filtered off via a sintered funnel. The filtrate was concentrated to dryness. The solid was taken up in heptane (1.0 L) and treated with methanol (96 g, 1.5 eq) at 20 to 40° C. to give crystals of the product. The solid product was collected via vacuum filtration through a Buchner funnel and washed with cold 15% ethyl acetate in heptane. The solid was taken up in ethyl acetate (1.5 L) and washed with brine, dried over sodium sulfate (200 g) and concentrated to give a white powder. Mp: 118 to 120° C., $^1$H NMR (400 MHz, CDCl$_3$) δ (ppm): −0.08 (s, 9H), 4.79 (d, J=4.4 Hz, 1H), 5.09 (dd, J=4.4, 2.7 Hz, 1H), 6.16 (bm, 1H), 7.3 to 7.4 (m, 5H).

EXAMPLE 17

Racemic Cis-N-T-Butoxycarbonyl-3-Trimethylsilyloxy-4-Phenyl-Azetidin-2-ONE

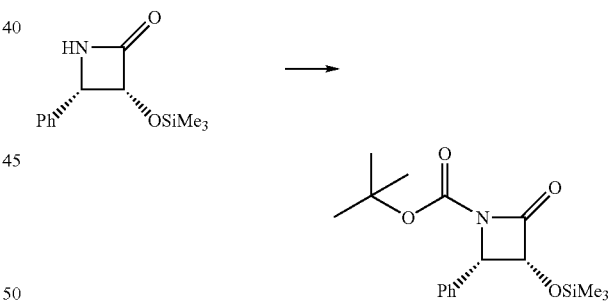

Racemic cis-3-trimethylsilyloxy-4-phenyl-azetidin-2-one (11.5 g, 48.9 mmol) was dissolved in tetrahydrofuran (THF, 250 mL) at ambient temperature under nitrogen and di-tert-butyldicarbonate was added along with N,N-4-dimethylaminopyridine (DMAP, 0.185 g, 1.5 mmol) and the mixture was magnetically stirred until the evolution of gas ceased. The mixture was filtered through a bed of silica gel (10 g) and concentrated on the rotary evaporator to give a white solid product. The product was washed with cold heptane (50 mL) and collected by vacuum filtration and dried to a constant weight of 12.3 g (75% yield) at ambient temperature and vacuum (0.2 mmHg). Mp: 75 to 77-C, $^1$H NMR (400 MHz, CDCl$_3$) δ (ppm): −0.07 (s, 9H), 1.38 (s, 9H), 5.01 (d, J=5.6 Hz, 1H), 5.06 (d, J=5.6 Hz, 1H), 7.26 to 7.38 (m, 5H).

EXAMPLE 18

Racemic (±)-Cis-N-T-Butoxycarbonyl-3-Diphenylmethylsilyloxy-4-Phenyl-Azetidin-2-One

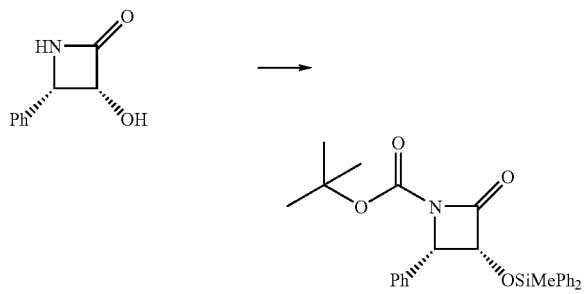

To a solution of racemic (±)-cis-3-hydroxy-4-phenyl-azetidin-2-one (4.5 g, 27.8 mmol) in THF (70 mL) under nitrogen was added triethylamine (8.4 g, 83.4 mmol), DMAP (100 mg, 0.83 mmol) and cooled to 0° C. Diphenylmethylsilyl chloride (7.1 g, 30.6 mmol) was added dropwise and the mixture was stirred at 0° C. for 30 min until complete disappearance of the starting material as shown by TLC eluting with 3:1 mixture of ethyl acetate and heptane. Di-tert-butyl-dicarbonate (Boc$_2$O, 6.68 g, 30.6 mmol) was added and the mixture was stirred at ambient temperature for 3 h for complete conversion to the desired product as shown by TLC (3:1 ethyl acetate:heptane). The mixture was diluted with heptane (150 mL) and filtered through silica gel (20 g) and the filtrate was concentrated to a solid. The solid was recrystallized from heptane (150 mL) to give a white powder (9.5 g, 74%). Mp 98° C., $^1$H NMR (400 MHz, CDCl$_3$) δ (ppm): 0.46 (s, 3H), 1.39 (s, 9H), 4.94 (d, J=5.5 Hz, 1H), 5.04 (d, J=5.5 Hz, 1H), 7.2 to 7.4 (m 15H).

EXAMPLE 19

Resolution of (±)-Cis-3-Hydroxy-4-(2-Furyl)-Azetidin-2-One (±)-Cis-3-hydroxy-4-(2-furyl)-azetidin-2-one (500 g, 3.265 mol) was treated with N-t-Boc-L-proline (378.83 g, 1.76 mol) in the presence of 0.5 equivalents of p-toluenesulfonyl chloride (335.53 g, 1.76 mol) and 1-methyl-imidazole (303.45 g, 3.7 mol) at −78° C. for 12 hours. The mixture was filtered through 5 kg of silica gel. The undesired (−)-β-lactam enantiomer of t-Boc-L-proline ester was removed by trituration with water. The desired enantiomer was recovered by azeotropic removal of the water with 2-methyl-1-propanol and recrystallized from ethyl acetate to give the desired (+)-cis-3-hydroxy-4-(2-furyl)-azetidin-2-one. The optical purity after recrystallizing from ethyl acetate was greater than 98%. mp: 133 to 135° C.; [α]$^{20}$ D=+109.5 (MeOH, c=1.0), $^1$H NMR (400 MHz, CDCl$_3$) (ppm): 2.69 (bs, 1H), 4.91 (d, J=4.96 Hz, 1H), 5.12 (bs, 1H), 6.10 (bs, 1H), 6.34 (dd, J=3.32, 3.32 Hz, 1H), 6.47 (d, J=3.32 Hz, 1H), 7.49 (m, 1H).

EXAMPLE 20

Resolution of (±)-Cis-3-Hydroxy-4-Phenyl-Azetidin-2-One (±)-cis-3-hydroxy-4-phenyl-azetidin-2-one (60 g, 0.368 mol) was treated with N-cBz-L-proline (45 g, 0.184 mol) in the presence of 0.5 equivalents of p-toluenesulfonyl chloride (35 g, 0.184 mol) and 1-methylimidazole (45 mL, 0.56 mol) at −78° C. for 12 hours. After concentration of the reaction mixture and filtration through silica gel to remove the 1-methylimidazolium tosylate salt, the desired diastereomer was crystallized from ethyl acetate to give 14.5 g (48%) of a white solid. This protocol resulted in kinetic resolution of the enantiomeric mixture to give the desired (+)-cis-3-hydroxy-4-phenyl-azetidin-2-one. The optical purity after recrystallizing from ethyl acetate was greater than 98%. mp: 175 to 180° C.; [α]$_{578}^{20}$=+202 (MeOH, c=1.0), $^1$H NMR (400 MHz, CDCl$_3$) (ppm): 2.26 (d, J=9.4 Hz, 1H), 4.96 (d, J=4.96 Hz, 1H), 5.12 (m, 1H), 4.15 (bm, 1H), 7.41 (m, 5H).

EXAMPLE 21

Kinetic Resolution of (±)-Cis-3-Hydroxy-4-Phenyl-Azetidin-2-One

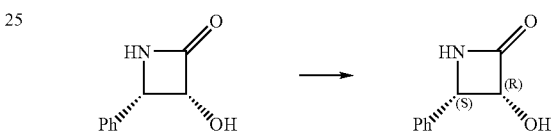

To a dry 250-mL round bottom flask under nitrogen was added acetonitrile (50 mL) and 1-methyl-imidazole (28 g, 0.2 mol) and the mixture was cooled to 0 to 5° C. Methanesulfonyl chloride (MsCl, 17.44 g, 0.1 mol) was added slowly to the mixture to control the exothermic reaction. After the reaction temperature was cooled to 0 −5° C., N-cBz-L-proline (25 g, 0.1 mol) was added and the mixture was stirred at this temperature for 30 min. In a separate 3-L flask under nitrogen, racemic (±)-cis-3-hydroxy-4-phenyl-azetidin-2-one (16.3 g, 0.1 mol) was dissolved in acetone (1 L) and cooled to −65 to −78° C. and stirred mechanically. Once the temperature reached below −65° C., the content of the flask containing the proline reagent was added to the acetone solution of the racemic starting material. The mixture was kept at this temperature for a minimum of 6 h and a white precipitate was observed. The precipitate was allowed to settle and supernatant was transferred to the rotary evaporator as a cold solution (circa −45° C.) via vacuum suction through an immersion filter. The acetone was removed and exchanged with ethyl acetate (500 mL) and triethylamine (50 g, 5 eq) base. The resulting salt was filtered off and the filtrate was concentrated to approximately 100 mL and crystal formation was allowed to occur. The crystals were collected via vacuum filtration through a Buchner funnel, washed with cold ethyl acetate, and dried under vacuum (0.1 mmHg) at ambient temperature to a constant weight of 7.5 g (46% yield).

The efficiency of the kinetic resolution was determined by the ratio of the diastereomeric ester (SSS:RRS) of the beta-lactam with the Boc-L-proline via $^1$HNMR according to Scheme 7. In Table 3, TsCl is tosyl chloride, Boc$_2$O is di-tert-butyldicarbonate, MsCl is mesyl chloride and MstCl is mesityl chloride.

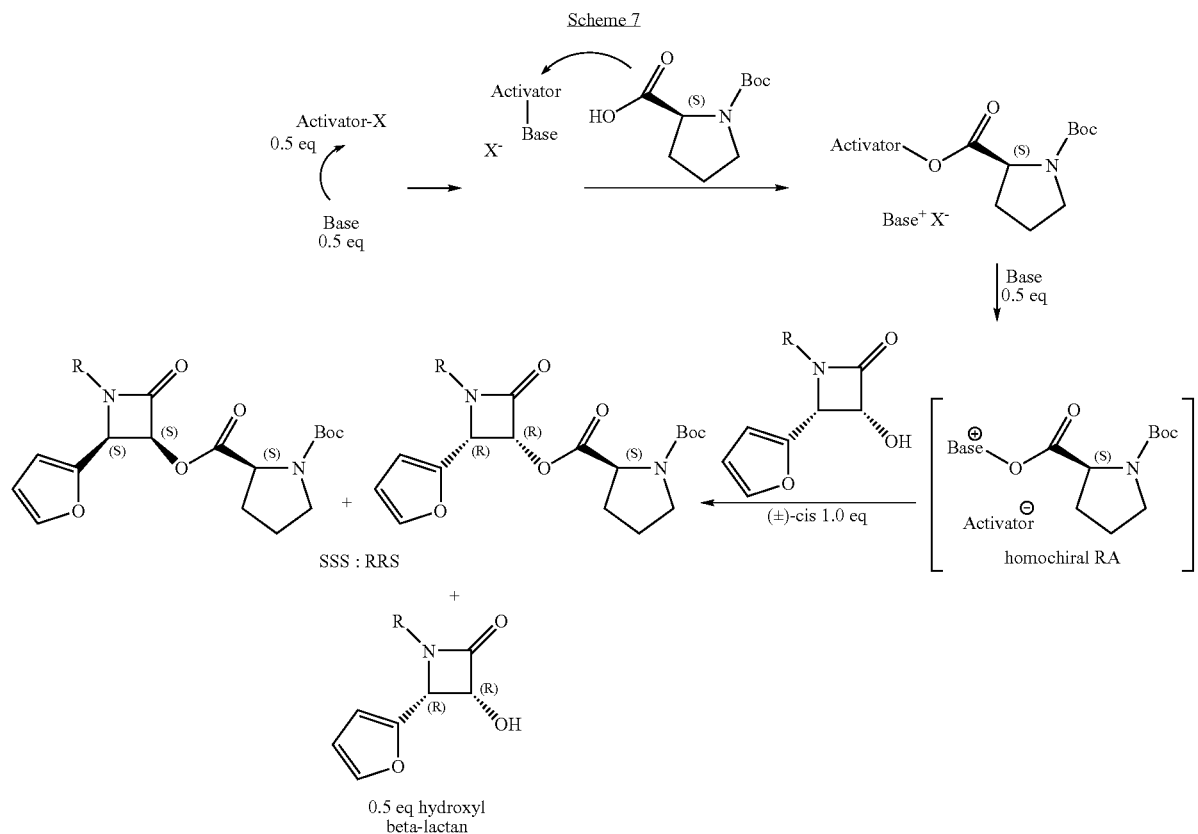

Scheme 7

TABLE 3

| Entry | R | Activator | Base | Temp (° C.) | Solvent | Time h/% Conv. | Dr SSS:RRS |
|---|---|---|---|---|---|---|---|
| 1 | PMP | TsCl | 1-methyl-imidazole | −78 | DME/ACN | 3/50 | 10:1 |
| 2 | H | TsCl | 1-methyl-imidazole | −78 | DME/ACN | 3/50 | 8.5:1 |
| 3 | H | TsCl | 1-methyl-imidazole | 0 | ACN | 3/50 | 2.6:1 |
| 4 | H | TsCl | triethylamine | 0 | ACN | 3/15 | 1:2.9 |
| 5 | H | TsCl | 1-methylbenzimidazole | −78 to 22 | DME/ACN | 12/50 | 8:1 |
| 6 | H | TsCl | 1,2-dimethylimidazole | −78 | DME/ACN | 3/50 | 4.5:1 |
| 7 | H | TsCl | Pyridine | −40 | Pyridine | 6/20 | 6.8:1 |
| 8 | H | TsCl | Pyridine | 0 | Pyridine | 3/50 | 3.8:1 |
| 9 | H | TsCl | DMAP | 0 | ACN | 3/50 | 1:1 |
| 10 | H | Boc$_2$O | 1-methyl-imidazole | 0 | ACN | 1/30 | 2:1 |
| 11 | H | MsCl | 1-methyl-imidazole | −40 | DME/ACN | 4/50 | 4.3:1 |
| 12 | H | MsCl | Pyridine | −40 | Pyridine | 6/10 | 5:1 |
| 13 | H | MstCl | 1-methyl-imidazole | −40 | DME/ACN | 12/50 | 4.3:1 |

EXAMPLE 22

Classical Resolution of (±)-Cis-3-Hydroxy-4-Phenyl-Azetidin-2-One

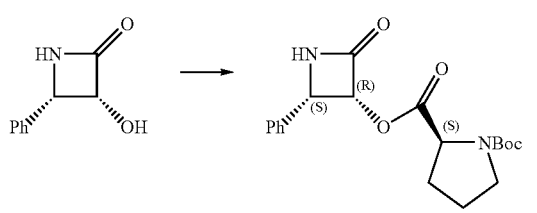

-continued

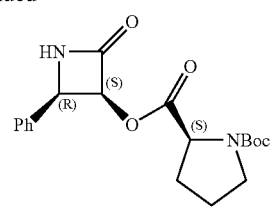

As an alternative to the above kinetic resolution, the diastereomeric mixture of the proline esters was separated via recrystallization from ethyl acetate. Subsequent hydrolysis of the proline esters separately would yield both enantiomers of the beta-lactam and recover the chiral amino acid. Thus, to a solution of N-methyl-imidazole (12 g, 150 mmol) in acetonitrile (80 mL) at 0° C. was added methanesulfonyl chloride (MsCl, 5.7 g, 50 mmol) and stirred for 15 minutes until the exothermic reaction temperature was stable at 0° C. To this solution was added N-Boc-L-Proline (11 g, 50 mmol) portion-wise and stirred at 0° C. for 30 minutes. Racemic (±)-cis-3-hydroxy-4-phenyl-azetidin-2-one (8.2 g, 50 mmol) was added portion-wise and the mixture was stirred at this temperature until TLC monitoring (3:1/ethyl acetate:hexanes) indicated complete conversion to the ester products after 1 h. The acetonitrile solvent was removed under rotary evaporation at 40° C. and the residue was taken up in ethyl acetate (500 mL), washed with water (100 mL), saturated aqueous sodium bicarbonate, brine, and dried over sodium sulfate. The drying agent was removed by vacuum filtration and the filtrate was concentrated to give 18 g of solid. A portion (7 g) of the mixture was taken up in 40° C. ethyl acetate (60 mL) and crystals (1.5 g) were formed at 40° C.; the crystals were collected and shown to be the desired 3R,4 S-diastereomer of the (2S)-tert-butyl(3R,4S)-2-oxo-4-phenylazetidin-3-yl pyrrolidine-1,2 -dicarboxylate. $^1$H NMR (400 MHz, CDCl$_3$) δ (ppm): This diastereomer exists as a 1.7:1 (δ (ppm)5.84:5.87) pair of diastereomers on the NMR timescale as typified by the characteristic chemical shift change of the starting material C3-carbinol proton from a multiplet at 5.12 ppm downfield to 5.8 ppm as a pair of doublet of doublets (J=4.68, 2.57 Hz) in the esterified product.

The filtrate was allowed to stand at ambient temperature for 5 h to give a second form of crystals (2.4 g) shown to be the 3S,4R-diastereomer of (2S)-tert-butyl (3S,4R)-2-oxo-4-phenylazetidin-3-yl pyrrolidine-1,2-dicarboxylate. $^1$H NMR (400 MHz, CDCl$_3$) δ (ppm): This diastereomer exists as a 1:1.9 (δ (ppm)5.90:5.94) pair of diastereomers on the NMR timescale as typified by the characteristic chemical shift change of the starting material C(3)-carbinol proton from a multiplet at 5.12 ppm downfield to 5.9 ppm as a pair of doublet of doublets (J=4.68, 2.57 Hz) in the esterified product.

Differences between the classical thermodynamic controlled resolution and the kinetic resolution are that a stoichiometric amount of reagents are used and careful low temperature control is not critical. However, classical resolution requires one additional step of de-esterification of the diastereomeric ester to recover the desired C3-hydroxy substituted β-lactam.

EXAMPLE 23

Optically Active (+)-Cis-3-Trimethylsilyloxy-4-Phenyl-Azetidin-2-one

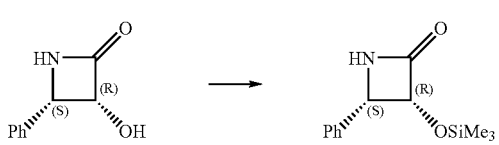

Optically active (+)-cis-3-hydroxy-4-phenyl-azetidin-2-one (3.4 g, 20.8 mmol) was dissolved in THF (30 mL) along with triethylamine (5.8 g, 57.4 mmol) and DMAP (76 mg, 0.62 mmol) at 0° C. Trimethylsilyl chloride (2.4 g, 22 mmol) was added dropwise and the mixture stirred for 30 min. TLC (3:1 ethyl acetate:heptane) showed complete conversion to the less polar product. The mixture was diluted with ethyl acetate (30 mL), washed with saturated aqueous sodium bicarbonate (15 ml), brine (15 ml), and dried over sodium sulfate (5 g). The sodium sulfate was filtered and the filtrate was concentrated and solvent exchanged with heptane (50 mL) to give a white powder. The powder was collected via vacuum filtration through a Buchner funnel and dried under vacuum (<1 mmHg) at ambient temperature to a constant weight of 3.45 g (72% yield). mp: 120 to 122° C., $[α]^{22}_{578}$=+81.9 (MeOH, 1.0), $^1$H NMR (400 MHz, CDCl$_3$) δ (ppm): −0.08 (s, 9H), 4.79 (d, J=4.4 Hz, 1H), 5.09 (dd, J=4.4, 2.7 Hz, 1H), 6.16 (bm, 1H), 7.3 to 7.4 (m, 5H).

EXAMPLE 24

Optically Active (+)-Cis-N-T-Butoxycarbonyl-3-Trimethylsilyloxy-4-Phenyl-Azetidin-2-One

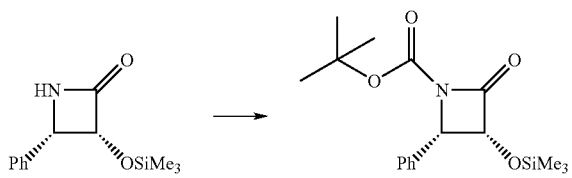

To a solution of optically active (+)-cis-3-trimethylsilyloxy-4 -phenyl-azetidin-2-one (0.95 g, 4 mmol) in THF (10 mL) was added triethylamine (1.1 g, 5 mmol), DMAP (15 mg, 0.12 mmol) and di-tert-butyldicarbonate (Boc$_2$O, 5.04 g, 5 mmol). The mixture was stirred at ambient temperature until the evolution of gas ceased and complete conversion to a less polar product was observed via TLC (2:1 ethyl acetate:heptane). The reaction mixture was diluted with heptane (20 mL) and filtered through a pad of silica gel (10 g) and concentrated in a 30° C. rotary evaporator until crystal formation occurred. The crystals were collected via vacuum filtration through a Buchner funnel, washed with cold heptane, and dried under vacuum (<1 mmHg) at ambient temperature to a constant weight of 0.87 g (65%). mp: 85 to 88° C., $[α]^{22}_{578}$=+106.9 (MeOH, 1.0), $^1$H NMR (400 MHz, CDCl$_3$) δ (ppm): −0.07 (s, 9H), 1.38 (s, 9H), 5.01 (d, J=5.6 Hz, 1H), 5.06 (d, J=5.6 Hz, 1H), 7.26 to 7.38 (m, 5H).

EXAMPLE 25

7,10-O-(1,1,3,3-Tetramethyl-1,3-Disiloxanediyl)-10-Dab

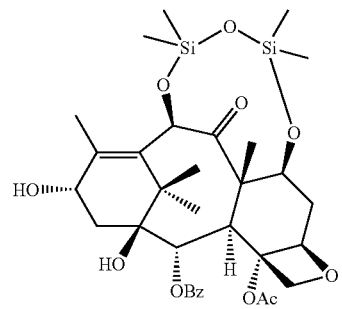

Typically, 10-DAB (108.96 g, 0.20 mol) was dissolved in THF at approximately 20 to 25 mL/g (2.2 L) along with 2.5 eq of DMAP (61.08 g, 0.5 mol). To this solution was added 1,3-dichloro-1,1,3,3-tetramethyldisiloxane (42.67 g, 0.21 mol) at ambient temperature until the conversion the product was complete by TLC (3:1 ethyl acetate/heptane). The reaction mixture then was diluted with heptane (2 L) to precipitate out the DMAP-HCl salt and filtered through silica gel (104.5 g). The filter cake was washed with a 1:1 mixture of ethyl acetate and heptane (800 mL) to ensure complete product recovery. The filtrate was stabilized with triethylamine (14 mL) and concentrated until crystals formed. The mixture was chilled to 0° C. for 30 min and the white solid was collected via a Buchner funnel and washed with ice-cold 20% ethyl acetate in heptane (500 mL). The filter cake was dried under vacuum (0.1 mmHg) at 50° C. to constant weight of 109 g. The filtrate was filtered thru silica gel and concentrated to give 13.2 g of a second crop of crystals. The total yield was 122.2 g (0.18 mol, 90%), at 99.2% HPLC purity. mp: 220 to 223° C. $^1$H NMR (400 MHz, CDCl$_3$) δ (ppm): 0.07 (s, 3H), 0.11 9 (s, 3H), 0.14 (s, 3H), 0.41 (s, 3H), 1.09 (s, 6H), 1.51 (s, 1H), 1.89 (ddd, J=13.9, 12.4,2.2 Hz, 1H), 1.99 (d, J=4.6 Hz) 1.56 (s, 3H), 2.04 (bs, 3H), 2.27 (m, 1H), 2.29 (s, 3H), 2.33 (m, 1H), 3.92 (d, 7.5 Hz, 1H), 4.19 (d, J=8.5 Hz, 1H), 4.3 (d, J=8.5 Hz, 1H), 4.51 (dd, J=10.6,6.7 Hz, 1H), 4.87 (bm, 1H), 4.95 (dd, J=9.4, 1.7 Hz, 1H), 5.60 (d, J=7.5, 1H), 5.61 (s, 1H), 7.48 (dd, J=7.8, 7.7 Hz, 2H), 7.6 (dd, J=7.8, 7.7 Hz, 1H)8.1 (d J=7.8, 2H).

EXAMPLE 26

7,10-O-(1,1,3,3-Tetramethyl-1,3-Ethanediyl)-10-Dab

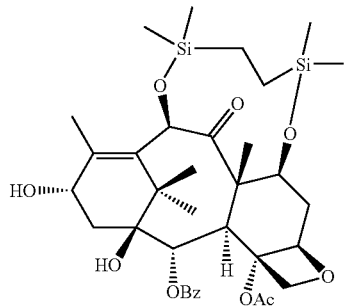

10-DAB (0.544 g, 1 mmol) was dissolved in THF at approximately 20 to 25 mL/g (10 mL) along with 2.5 eq of DMAP (0.3 g, 2.5 mmol). To this solution was added 1,2-bis(chlorodimethylsilyl)ethane (0.215 g, 1 mol) at ambient temperature until the conversion of the product was complete by TLC (3:1 ethyl acetate/heptane). The reaction mixture then was diluted with heptane (20 mL) to precipitate out the DMAP-HCl salt and filtered through silica gel (10 g). The filter cake was washed with a 1:1 mixture of ethyl acetate and heptane (20 mL) to ensure complete product recovery. The filtrate was stabilized with triethylamine (0.5 mL) and concentrated until crystals formed. The mixture was chilled to 0° C. for 30 min and the white solid was collected via a Buchner funnel and washed with ice-cold 20% ethyl acetate in heptane (10 mL). The filter cake was dried under vacuum (0.1 mmHg) at 50° C. to constant weight of 0.58 g (85% yield). Mp: 191 to 193° C., $^1$H NMR (400 MHz, CDCl$_3$) δ (ppm): 0.05 (s, 3H), 0.9 (s, 3H), 0.17 (s, 3H), 0.33 (s, 3H), 0.43 (m, 1H), 0.57 (dd, J=11.8, 5.6 Hz, 2H), 0.78 (m, 1H), 1.05 (s, 3H), 1.10 (s, 3H), 1.54 (s, 1H), 1.69 (s, 3H), 1.87 (m, J=14.1, 12.6, 4.2, 1.9 Hz, 1H), 2.06 (d, J=1.2 Hx, 3H), 2.11 (d, J=5.0 Hz, 1H), 2.26 (m 1H), 2.27, (s, 3H), 2.32 (m, 1H), 3.92 (d, J=6.8 Hz, 1H), 4.15 (d, J=8.5), 4.28 (d, J=8.5 Hz), 4.31 (dd, J=10.1, 6.5 Hz, 1H), 4.84 (m, 15.2, 5.4, 7.7 Hz), 4.92 (dd, J=9.7, 2.0 Hz, 1H), 5.46 (s, 1H), 5.57 (d, J=7.3, 1H), 7.48 (dd, J=7.8,7.7 Hz, 2H), 7.6 (dd, J=7.8, 7.7 Hz, 1H)8.1 (d J=7.8, 2H).

EXAMPLE 27

7,10-O-(1,1,3,3,5,5-Hexamethyl-1,3,5-Trisiloxanediyl)-10-Dab

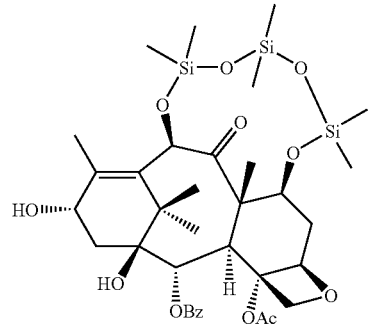

10-DAB (0.544 g, 1 mmol) was dissolved in THF at approximately 20 to 25 mL/g (10 mL) along with 2.5 eq of DMAP (0.3 g, 2.5 mmol). To this solution was added 1,5-dichlorohexamethyltrisiloxane (0.277 g, 1 mol) at ambient temperature until the conversion the product was complete by TLC (3:1 ethyl acetate/heptane). The reaction mixture then was diluted with heptane (20 mL) to precipitate out the DMAP-HCl salt and filtered through silica gel (10 g). The filter cake was washed with a 1:1 mixture of ethyl acetate and heptane (20 mL) to ensure complete product recovery. The filtrate was stabilized with triethylamine (0.5 mL) and concentrated until crystals formed. The mixture was chilled to 0° C. for 30 min and the white solid was collected via a Buchner funnel and washed with ice-cold 20% ethyl acetate in heptane (10 mL). The filter cake was dried under vacuum (0.1 mmHg) at 50° C. to constant weight of 0.65 g (87% yield). Mp: 240 to 242° C., $^1$H NMR (400 MHz, CDCl$_3$) δ (ppm): 0.06 (s, 6H), 0.09 (1, 3H), 0.15 (s, 3H), 0.16 (s, 3H), 0.29 (s, 3H), 1.05 (s, 3H), 1.19 (s, 3H), 1.56 (s, 1H), 1.70 (s, 3H), 1.89 (m, 1H), 1.96 (d, J=5.3 Hz, 1H), 2.10 (d, J=1.0 Hz, 3H), 2.27 (m, 1H), 2.29 (s, 3H), 2.42 (m, 1H), 3.96 (d, J=7.1 Hz, 1H), 4.17 (d, J=8.1 Hz, 1H), 4.29 (d, J=8.1 Hz, 1H), 4.49 (dd, J=10.0, 6.9 Hz, 1H), 4.85 (m, 1H), 4.94 (dd, J=9.6, 1.9 Hz, 1H), 5.63 (s, 1H), 5.64 (d, 6.75 Hz, 1H), 7.47 (dd, J=7.8,7.7 Hz, 2H), 7.59 (dd, J=7.8, 7.7 Hz, 1H)8.11 (d J=7.8, 2H).

EXAMPLE 28

Docetaxel

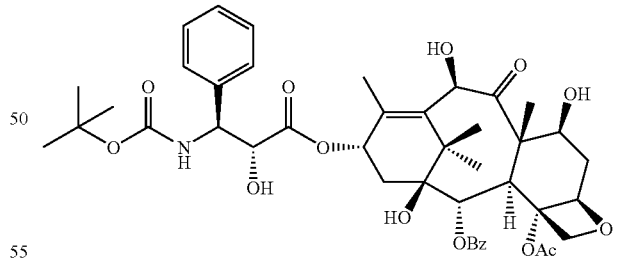

Starting with 10-DAB, the C(7) and C(10) hydroxy groups were protected using 1,3-dichlorotetramethyldisiloxane (i.e., the bridging silicon-based protecting group of Formula (4) wherein $G_1$, $G_2$, $G_3$, and $G_4$ are methyl, $L_1$ and $L_2$ are chloro, Z is —O—); cyclic intermediate (29) wherein $G_1$, $G_2$, $G_3$, and $G_4$ are methyl, Z is —O—) resulted in 95% yield after recrystallization from ethyl acetate and heptane. The coupling of intermediate (29) and β-lactam side chain precursor (36) wherein $P_2$ is MOP was carried out under kinetic resolution using LHMDS and 3 equivalents of the racemic (36); intermediate (410) wherein $G_1$, $G_2$, $G_3$, and $G_4$ are methyl, $P_2$ is MOP, Z is —O—) resulted in 90% yield after recrystallization from dichloromethane and heptane. Simple dilute hydrochloric acid deprotection gave docetaxel in 75% yield after recrystallization from isopropanol and heptane.

EXAMPLE 29

2'-(2-Methoxy-2-Propoxy)-7,10-O-(1,1,3,3-Tetramethyl-1,3-Disiloxanediyl)-Docetaxel

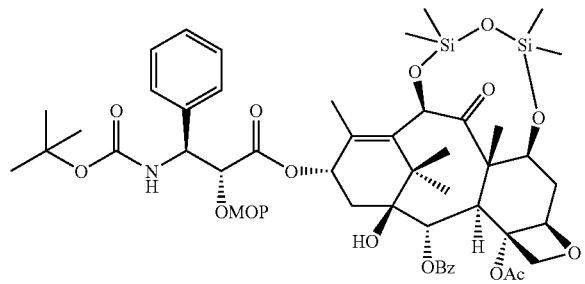

7,10-O-(1,1,3,3-tetramethyl-1,3-disiloxanediyl)-10-DAB (0.67 g, 0.99 mmol) and cis-N-t-butoxy-3-(2-methoxy-2-propoxy)-4-phenyl-azetidin-2-one (1.0 g, 3 eq) was dissolved in anhydrous THF (5 mL) under nitrogen then cooled to −45° C. LHMDS (1.2 mL, 1.1 eq) 1.0 M in THF was added drop-wise to control the exotherm. The reaction was allowed to proceed at ≦−35° C. for 2 to 5 h. The reaction was quenched with a solution of acetic acid (1.2 eq) in ethyl acetate (25 mL), washed with sodium bicarbonate (5 mL) and brine (5 mL), dried over sodium sulfate (7 g), filtered through silica (7 g), and concentrated. The residue was taken up in a minimal amount of dichloromethane (1 mL) containing 1% triethylamine and added to heptane (15 mL) to triturate out the excess β-lactam. The product (0.88 g, 88%) as a single diastereomer was collected by Buchner funnel and washed with heptane. Mp: 235 to 238° C., $^1$H NMR (MHz, CDCl$_3$) δ (ppm): 0.07 (s, 3H), 0.08 (s, 3H), 0.12 (s, 3H), 0.41 (s, 3H), 1.08 (s, 3H), 1.12 (s, 3H), 1.25 (s, 3H), 1.30 (s, 3H), 1.32 (s, 9H), 1.53 (s, 1H), 1.67 (s, 3H), 1.90 (bs, 3H), 1.92 (m, 1H), 2.07 (m, 1H), 2.30 (m, 2H), 2.50 (s, 3H), 2.66 (bs, 3H), 3.84 (d, J=6.9 Hz, 1H), 4.22 (d, J=8.7 Hz, 1H), 4.32 (d, J=8.7 Hz, 1H), 4.48 (dd, J=9.9, 6.4 Hz, 1H), 4.50 (d, J=3.3 Hz, 1H), 4.95 (m, J=8.6, 1H), 5.22 (bm, 1H), 5.49 (bm, 1H), 5.57 (s, 1H), 5.65 (d, J=6.9 Hz, 1H), 6.24 (bm, 1H), 7.24 (m, 1H), 7.30 (d, J=7.2, 2H), 7.37 (dd, J=7.2, 7.2, 2H), 7.51 (dd, J=8.0, 7.5 Hz, 2H), 7.60 (dd, J=8.0, 7.2 Hz, 1H), 8.11 (d, J=7.5 Hz, 2H). The flexible side chain proton chemical shifts exhibit drifting dependent on level of water in the CDCl$_3$ solvent.

EXAMPLE 30

Docetaxel

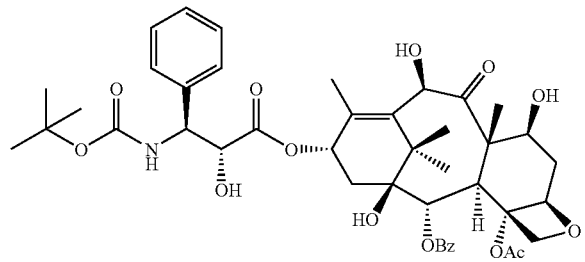

2'-(2-methoxy-2-propoxy)-7,10-O-(1,1,3,3-tetramethyl-1,3-disiloxanediyl)-docetaxel (38.38 g, 38.2 mmol) in acetonitrile (580 mL) then 0.2 M HCl (115 mL) was added and the mixture was stirred at ambient temperature (22° C. to 25° C.) for 2 to 3 h until complete conversion to the product (R$_f$=0.15) was observed via TLC (3:1 ethyl acetate:heptane). The product mixture then was diluted with ethyl acetate (580 mL) and washed with water (290 mL), brine (150 mL), saturated aqueous sodium bicarbonate (290 mL), brine (200 mL) and dried over sodium sulfate (60 g). The mixture was filtered through silica gel (30 g) and the filter cake was rinsed with ethyl acetate (350 mL). The combined filtrate was concentrated to approximately 192 mL followed by addition of heptane (550 mL) to induce crystallization. The mixture was further concentrated to remove approximately 200 mL of solvent. The mixture was cooled to ambient temperature, the crystals were collected via vacuum filtration through a Buchner funnel, and the crystals were dried to a constant weight of 30.57 g (99.3% yield) at 98.3% HPLC purity. mp: 186 to 188° C., EA: % C: theory 63.93, found 63.38, % H: theory 6.61, found 6.59. $^1$H NMR (400 MHz, CDCl$_3$) δ (ppm): 1.13 (s, 3H, H-17), 1.24 (s, 3H, H-16), 1.34 (s, 9H, H-t-Boc), 1.64 (s, 1H, HO-1), 1.76 (s, 3H, H-19), 1.85 (s, 3H, H-18), 1.79 to 1.88 (m, 1H, H-6), 2.27 (m, J=8.8 Hz, 2H, H-14), 2.38 (s, 3H, Ac-4), 2.60(m, 1H, H-6), 3.32 (bd, J=4.8 Hz, 1H, HO-2'), 3.92 (d, J=6.9 Hz, 1H, H-3), 4.18 (d, J=8.5 Hz, 1H, H-20), 4.19 (bs, 1H, HO-10), 4.23 (m, 1H, H-7), 4.32 (d, J=8.5 Hz, 1H, H-20), 4.62 (bm, 1H, H-2'), 4.94 (m, 1H, H-5), 5.20 (bd, J=1.7 Hz, H-10), 5.26 (bm, 1H, H-3'), 5.40 (bd, J=9.6 Hz, H—N), 5.68 (d, J=6.9 Hz, 1H, H-2), 6.22 (bm, 1H, H-13), 7.29 to 7.4 (m, 5H, H—Ph), 7.50 (dd, J=7.9, 7.6 Hz, 2H, H-mBz), 7.62 (dd, J=7.25, 7.6 Hz, 1H-pBz), 8.10 (d, J=7.9 Hz, 2H, H-oBz). Conformed to Literature References: (a) Journal of Labelled Compounds and Radiopharmaceuticals, 2004; 47:763-777; and (b) Tetrahedron, 1989, 45:13, pp 4177-4190.

EXAMPLE 31

2'-(Trimethylsilyloxy)-7,10-O-(1,1,3,3-Tetramethyl-1,3-Disiloxanediyl)-Docetaxel

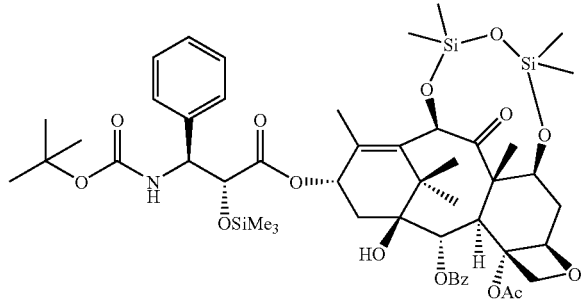

7,10-O-(1,1,3,3-tetramethyl-1,3-disiloxanediyl)-10-DAB (4.29 g, 6.4 mmol) and N-t-butoxycarbonyl-3-trimethylsilyloxy-4-phenyl azetidin-2-one (6.4 g, 19.1 mmol) were dissolved in anhydrous THF (43 mL) under nitrogen and then cooled to −45° C. LHMDS (1.2 mL, 1.1 eq, 1.0 M in THF) was added drop-wise to control the exotherm. The reaction was allowed to proceed at ≦−45° C. for 5 h. The reaction was quenched with a solution of acetic acid (1.2 eq) in ethyl acetate (50 mL), washed with sodium bicarbonate (10 mL) and brine (10 mL), dried over sodium sulfate (10 g), filtered through silica (10 g), and concentrated to give a solid. The solid was recrystallized from methanol to give 3.6 g (55%) of white powder as a single diastereomer after drying under vacuum (<1 mmHg) and ambient temperature. mp: 248 to 250° C., $^1$H NMR (400 MHz, CDCl$_3$) δ: −0.12 (s, 9H), 0.08 (s, 3H), 0.09 (s, 3H), 0.12 (s, 3H), 0.42 (s, 3H), 1.12 (s, 3H), 1.27 (s, 3H), 1.31 (s, 9H), 1.54 (s, 1H), 1.68 (s, 3H), 1.88 (s, 3H), 1.86 to 1.96 (m, 1H), 2.08 to 2.18 (m, 1H), 2.26 to 2.43 (m, 2H), 2.54 (s, 3H), 3.85 (d, J=7.2 Hz, 1H), 4.24 (d, J=8.5 Hz, 1H), 4.32 (d, J=8.5 Hz, 1H), 4.45 (bs, 1H), 4.50 (dd, J=6.8, 10.3 Hz, 1H), 4.96 (m, J=8.5 Hz, 1H), 5.29 (m, J=8.5 Hz, 1H), 5.52 (bm, J=8.5 Hz, 1H), 5.57 (s, 1H), 5.66 (d, J=7.5 Hz, 1H), 6.31 (bt, J=8.6 Hz, 1H), 7.3 to 7.41 (m, 5H), 7.48 (dd, J=6.9, 8.4 Hz, 2H,) 7.59 (dd, J=6.9, 7.5, 1H), 8.12 (d, J=7.5 Hz, 2H).

EXAMPLE 32

2'-(Trimethylsilyloxy)-7,10-O-(1,1,3,3-Tetramethyl-1,3-Disiloxanediyl)-Docetaxel To a solution of 7,10-O-(1,1,3,3-tetramethyl-1,3-disiloxanediyl)-10-DAB (0.84 g, 1.24 mmol) in THF (10 mL) at −45° C. under nitrogen was added 1.0 M butyllithium (0.93 mL) in hexanes. After 30 min at this temperature, a solution of (+)—N-t-butoxycarbonyl-3-trimethylsilyloxy-4-phenyl azetidin-2-one (0.5 g, 1.5 mmol) in THF (2 mL) was added and the mixture was stirred and warmed to 0° C. over 4 h. The reaction was quenched with triethylamine (1 eq) and acetic acid (1 eq), diluted with 25 mL of heptane, and filtered through silica gel (30 g). The filtrate was concentrated by rotary evaporation to give white crystals (0.69 g, 55%) $^1$HNMR of the crude product conformed to the structure of 2'-(trimethylsilyloxy)-7,10-O-(1,1,3,3-tetramethyl-1,3-disiloxanediyl)-docetaxel.

EXAMPLE 33

Deprotection of 2'-(Trimethylsilyloxy)-7,10-O-(1,1,3,3-Tetramethyl-1,3-Disiloxanediyl)-Docetaxel To a solution of 2'-(trimethylsilyloxy)-7,10-O-(1,1,3,3-tetramethyl-1,3-disiloxanediyl)-docetaxel (0.5 g, 0.495 mmol) in acetonitrile (2.5 mL) at ambient temperature was added a solution of 0.2 M HCl and the mixture was stirred at ambient temperature (22° C. to 25° C.) for 2 to 3 h until complete conversion to the product ($R_f$=0.15) was observed via TLC (3:1 ethyl acetate:heptane). The mixture then was diluted with ethyl acetate (5 mL) and washed with water (2 mL), brine (2 mL), saturated aqueous sodium bicarbonate (2 mL), brine (2 mL) and dried over sodium sulfate (6 g). The mixture was filtered through silica gel (5 g) and the filter cake was rinsed with ethyl acetate (5 mL). The combined filtrate was concentrated to approximately 1 mL and heptane (5 mL) was added to induce crystallization. The mixture then was concentrated to remove approximately 1-2 mL of solvent. The mixture was cooled to ambient temperature before the crystals were collected via vacuum filteration through a Buchner funnel and dried to a constant weight of 0.399 g (93% yield) of a crystalline product with HNMR spectra that conformed to Docetaxel.

In order of maximize the recovery of Docetaxel it was discovered that purification of the intermediate 2'-(trimethylsilyloxy)-7,10-O-(1,1,3,3-tetramethyl-1,3-disiloxanediyl)-docetaxel was unnecessary when optically pure (+)—N-t-butoxycarbonyl-3-trimethylsilyloxy-4-phenyl azetidin-2-one was used.

EXAMPLE 34

Docetaxel

To an oven dried 25 mL round bottom flask (RBF) under nitrogen equipped with magnetic stirring was added diisopropylamine (0.83 mL, 5.86 mmol) and THF (1.5 mL). The mixture was cooled to −45° C. and a solution of n-hexyl lithium (2.33 mL, 2.30 M, 5.37 mmol) was added drop-wise to control the exotherm and maintain the reactor temperature at <−40° C. After the addition was completed, the cooling bath temperature was raised to 0-5° C. before use.

Coupling reaction: To an oven dried 250 mL RBF under nitrogen equipped with magnetic stirring was added 7,10-O-(1,1,3,3-tetramethyl-1,3-disiloxanediyl)-10-DAB (3.29 g, 4.88 mmol), and THF (30 mL). The mixture was cooled to 45° C. The already prepared LDA was added to the reaction mixture via syringe in a period of 5 minutes and stirred at that temperature for 45 minutes. To this mixture was then added (+)—N-t-butoxycarbonyl-3-trimethylsilyloxy-4-phenyl azetidin-2-one (1.80 g, 5.37 mmol) in THF (8 mL)). The reaction mixture was warmed up to −15° C. and stirred for one hour at −15 to −10° C. TLC monitoring of the reaction after one hour (1:3 ethyl acetate heptane) showed complete conversion to 2'-(trimethylsilyloxy)-7,10-O-(1,1,3,3-tetramethyl-1,3-disiloxanediyl)-docetaxel.

Work-up: To the reaction flask at reaction temperature was added 1 mL of saturated sodium bicarbonate and stirred for 5 minutes. It was then diluted by ethyl acetate (50 mL) and washed with 50 mL of brine. The organic layer was separated and dried over $MgSO_4$ and concentrated to give 5.10 g of crude 2'-(trimethylsilyloxy)-7,10-O-(1,1,3,3-tetramethyl-1,3-disiloxanediyl)-docetaxel that was used directly for deprotection. The above crude mixture was dissolved in acetonitrile (50 mL) and 0.2 N HCl (25 mL) was added and stirred at room temperature for four hours. TLC monitoring (3:1/EtOAc:heptane) showed the completion of the reaction. The reaction mixture was diluted by ethyl acetate (100 mL) and washed twice with distilled water (50 mL), saturated sodium bicarbonate (50 mL) and brine (50 mL). The resulting organic layer was dried over $MgSO_4$ and concentrated to give 3.76 g (95.3% yield) of Docetaxel with 96.5% HPLC purity with the major impurity as undesilylated (1.6%) intermediate at the C(7)-hydroxy group.

EXAMPLE 35

7-O-(1-Methoxy-1,1,3,3-Tetramethyl-1,3-Disiloxanyl)-10-DAB

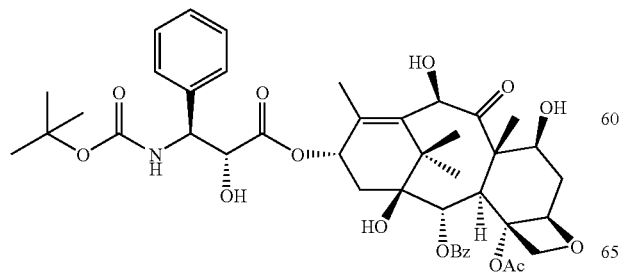

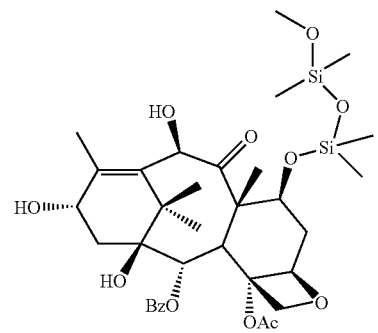

Triethylamine-methanolysis: To 1 g (1.48 mmol) of 7,10-O-(1,1,3,3-tetramethyl-1,3-disiloxanediyl)-10-DAB was added 20 mL of anhydrous methanol. The solution was allowed to stir until homogeneous (about 10 minutes). The flask was charged with 1 equivalent of triethylamine (TEA, 1.48 mmol, 206 mL) and allowed to stir for approximately 23 hours. Reaction completion was monitored with TLC (1:1 ethyl acetate:hexanes). Upon completion, the solution was diluted with about 15 mL heptane and evaporated until all the methanol was removed. Crystals formed on evaporation and were allowed to stir for 2 hours. Crystals were filtered and washed with heptane to yield 948 mg (90.6% yield) of a white solid. $^1$H NMR (400 MHz, CDCl$_3$) δ (ppm): 0.085 (s, 3H), 0.099 (s, 3H), 0.120 (s, 3H), 0.0123 (s, 3H), 1.09 (overlap, 2-s (6H), 1.75 (s, 3H), 1.93 (m, 1H), 1.97 (d, J=5.07 Hz, 1H), 2.09 (d, J=1.22 Hz, 3H), 2.27 (m, 1H), 2.28 (s, 3H), 2.55 (m, 1H), 3.48 (s, 3H), 3.98 (d, J=6.86 Hz, 1H), 4.18 (d, J=8.14 Hz, 1H), 4.25 (d, J=2.03 Hz, 1H), 4.31 (d, J=8.14 Hz, 1H), 4.49 (dd, J=10.91, 6.71 Hz, 1H), 4.88 (dd, 17.60, 7.48 Hz, 1H), 4.95 (dd, J=9.49, 1.79 Hz, 1H), 5.18 (d, J=2.03, 1H), 5.62 (d, J=6.94 Hz, 1H), 7.48(t, J=7.7–Hz, 2H), 7.60 (m, J=7.7 Hz, 1H), 8.11 (m, 2H).

As illustrated in the above examples, using 10-DAB and a β-lactam side chain precursor, docetaxel was prepared in high yield. This is highlighted by the novel use of a bridging silicon-based protecting group which was easily removed as compared to other protecting groups. Other analogous bridging silicon-based protecting groups gave similar yields of the 7,10-protected 10-DAB derivatives, including those listed in Table 4.

TABLE 4

| Formula Name | Structure |
| --- | --- |
| 1,5-dichlorohexamethyltrisiloxane | 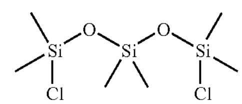 |
| 1,3-dichloro-1,3-diphenyl-1,3-dimethyldisiloxane | 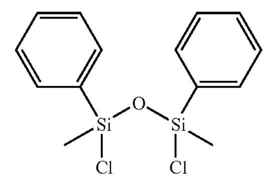 |
| 1,3-dichlorotetraphenyldisiloxane | 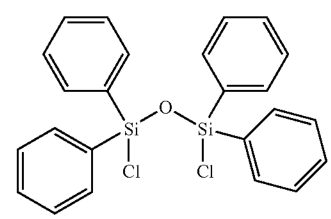 |
| 1,3-divinyl-1,3-dimethyl-1,3-dichlorodisiloxane | 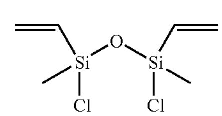 |
| 1,1,3,3-tetraisopropyl-1,3-dichlorodisiloxane | 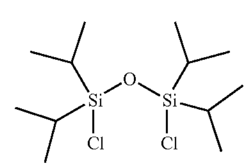 |
| 1,2-bis(chlorodimethylsilyl)ethane | 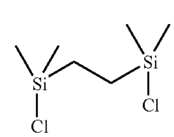 |

What is claimed is:

1. A process for the preparation of docetaxel, the process comprising:
   (a) protecting the C(7) and the C(10) hydroxy groups of 10-deacetylbaccatin III (10-DAB) with a bridging silicon-based protecting group to form 10-DAB derivative (12);
   (b) treating 10-DAB derivative (12) with a β-lactam side chain precursor to form 10-DAB derivative (13); and
   (c) deprotecting 10-DAB derivative (13) to form docetaxel; wherein
   10-DAB derivative (12) and 10-DAB derivative (13) correspond to Formulae (12) and (13), respectively:

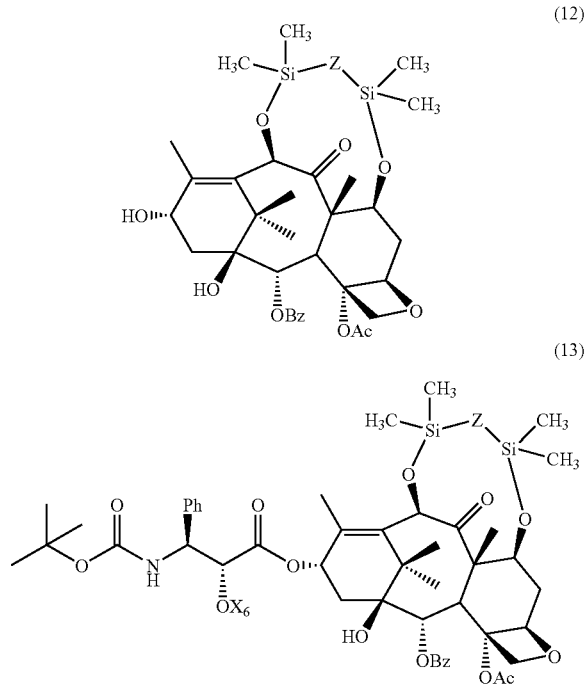

the bridging silicon-based protecting group corresponds to Formula (2):

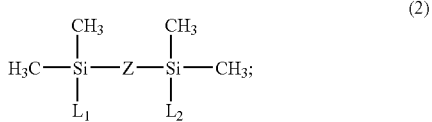

the β-lactam side chain precursor corresponds to Formula (3):

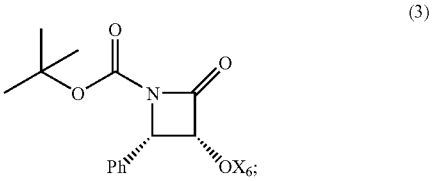

$L_1$ and $L_2$ are amine, bromo, chloro, iodo, or sulfonate leaving groups;

$X_6$ is a hydroxy protecting group; and
Z is —CH$_2$—CH$_2$—, —O—Si(CH$_3$)(CH$_3$)—O—, or —O—.

2. The process of claim 1 wherein the bridging silicon-based protecting group is selected from the group consisting of 1,3-dichlorotetramethyldisiloxane; 1,5-dichlorohexamethyltrisiloxane; and 1,2-bis(chlorodimethylsilyl)ethane;

3. The process of claim 1 wherein $X_6$ is 2-methoxy-2-propyl (MOP).

4. The process of claim 1 wherein the β-lactam side chain precursor corresponding to Formula (3) is prepared by a process comprising:
   (a) forming an N-unsubstituted β-lactam (8) having a silyloxy substituent, —OSiR$_{21}$R$_{22}$R$_{23}$, at the C(3) ring carbon atom by: (i) reacting benzaldehyde with a disilazide to form an imine; and (ii) treating the imine with a ketene acetal to form the N-unsubstituted β-lactam (8);
   (b) replacing the —SiR$_{21}$R$_{22}$R$_{23}$ moiety of the silyloxy substituent with a hydroxy protecting group, $X_6$; and (c) introducing a tert-butoxycarbonyl group to the —NH moiety to form the β-lactam side chain precursor corresponding to Formula (3); wherein
   the N-unsubstituted β-lactam corresponds to Formula (8):

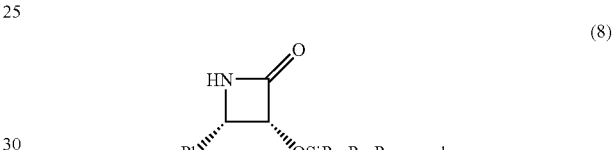

$R_{21}$, $R_{22}$, and $R_{23}$ are independently alkyl, aryl, or aralkyl.

5. The process of claim 4 wherein the N-unsubstituted β-lactam (8) formed in step (a)(ii) is present as an enantiomeric mixture of first and second C(3)-silyloxy substituted β-lactam enantiomers and the process for producing the β-lactam side chain precursor corresponding to Formula (3) further comprises replacing the —SiR$_{21}$R$_{22}$R$_{23}$ moiety of the silyloxy substituent with a hydrogen atom to form an enantiomeric mixture of first and second C(3)-hydroxy substituted β-lactam enantiomers and resolving the enantiomeric mixture of first and second C(3)-hydroxy substituted β-lactam enantiomers, the resolution comprising:
   (a) treating the enantiomeric mixture of first and second C(3)-hydroxy substituted β-lactam enantiomers with an optically active proline acylating agent in the presence of an amine to form a product mixture, the product mixture containing first and second C(3)-ester substituted β-lactam diastereomers formed by reaction of the first and second C(3)-hydroxy substituted β-lactam enantiomers, respectively, with the optically active proline acylating agent, the product mixture optionally also containing unreacted second C(3)-hydroxy β-lactam enantiomer, and
   (b) separating the first C(3)-ester substituted β-lactam diastereomer from the unreacted second C(3)-hydroxy β-lactam enantiomer or the second C(3)-hydroxy substituted β-lactam diastereomer.

6. The process of claim 1 wherein Z is —CH$_2$—CH$_2$—.
7. The process of claim 1 wherein Z is —O—Si(CH$_3$)(CH$_3$)—O—.
8. The process of claim 1 wherein Z is —O—.
9. The process of claim 1 wherein $L_1$ and $L_2$ are amine leaving groups.
10. The process of claim 1 wherein $L_1$ and $L_2$ are imidazole, diethylamine, or diisopropylamine leaving groups.

11. The process of claim 1 wherein $L_1$ and $L_2$ are bromo, chloro, or iodo leaving groups.

12. The process of claim 1 wherein $L_1$ and $L_2$ are chloro leaving groups.

13. The process of claim 1 wherein $L_1$ and $L_2$ are sulfonate leaving groups.

14. The process of claim 1 wherein $L_1$ and $L_2$ are tosylate, triflate, or mesylate leaving groups.

15. The process of claim 1 wherein Z is —$CH_2$—$CH_2$— and $L_1$ and $L_2$ are amine leaving groups.

16. The process of claim 1 wherein Z is —$CH_2$—$CH_2$— and $L_1$ and $L_2$ are imidazole, diethylamine, or diisopropylamine leaving groups.

17. The process of claim 1 wherein Z is —$CH_2$—$CH_2$— and $L_1$ and $L_2$ are bromo, chloro, or iodo leaving groups.

18. The process of claim 1 wherein Z is —$CH_2$—$CH_2$— and $L_1$ and $L_2$ are chloro leaving groups.

19. The process of claim 1 wherein Z is —$CH_2$—$CH_2$— and $L_1$ and $L_2$ are sulfonate leaving groups.

20. The process of claim 1 wherein Z is —$CH_2$—$CH_2$— and $L_1$ and $L_2$ are tosylate, triflate, or mesylate leaving groups.

21. The process of claim 1 wherein Z is —O—$Si(CH_3)(CH_3)$—O— and $L_1$ and $L_2$ are amine leaving groups.

22. The process of claim 1 wherein Z is —O—$Si(CH_3)(CH_3)$—O— and $L_1$ and $L_2$ are imidazole, diethylamine, or diisopropylamine leaving groups.

23. The process of claim 1 wherein Z is —O—$Si(CH_3)(CH_3)$—O— and $L_1$ and $L_2$ are bromo, chloro, or iodo leaving groups.

24. The process of claim 1 wherein Z is —O—$Si(CH_3)(CH_3)$—O— and $L_1$ and $L_2$ are chloro leaving groups.

25. The process of claim 1 wherein Z is —O—$Si(CH_3)(CH_3)$—O— and $L_1$ and $L_2$ are sulfonate leaving groups.

26. The process of claim 1 wherein Z is —O—$Si(CH_3)(CH_3)$—O— and $L_1$ and $L_2$ are tosylate, triflate, or mesylate leaving groups.

27. The process of claim 1 wherein Z is —O— and $L_1$ and $L_2$ are amine leaving groups.

28. The process of claim 1 wherein Z is —O— and $L_1$ and $L_2$ are imidazole, diethylamine, or diisopropylamine leaving groups.

29. The process of claim 1 wherein Z is —O— and $L_1$ and $L_2$ are bromo, chloro, or iodo leaving groups.

30. The process of claim 1 wherein Z is —O— and $L_1$ and $L_2$ are chloro leaving groups.

31. The process of claim 1 wherein Z is —O— and $L_1$ and $L_2$ are sulfonate leaving groups.

32. The process of claim 1 wherein Z is —O— and $L_1$ and $L_2$ are tosylate, triflate, or mesylate leaving groups.

\* \* \* \* \*